US005962469A

United States Patent [19]
Thomas et al.

[11] Patent Number: 5,962,469
[45] Date of Patent: Oct. 5, 1999

[54] CYCLIC NITRONES

[75] Inventors: Craig E. Thomas; Thomas L. Fevig, both of West Chester; Stephen M. Bowen, Cincinnati; Robert A. Farr, Loveland; Albert A. Carr, Cincinnati, all of Ohio; David A. Janowick, Beach Park, Ill.

[73] Assignee: Hoechst Marion Roussel Inc., Cincinnati, Ohio

[21] Appl. No.: 08/978,971

[22] Filed: Nov. 26, 1997

Related U.S. Application Data

[63] Continuation of application No. 08/700,588, Aug. 16, 1996, abandoned
[60] Provisional application No. 60/003,551, Sep. 11, 1995.

[51] Int. Cl.$^6$ ............... C07D 221/06; C07D 491/02; A61K 31/44; A61K 31/47
[52] U.S. Cl. ............ 514/301; 514/278; 514/290; 514/302; 514/307; 514/309; 546/18; 546/101; 546/110; 546/114; 546/115; 546/116; 546/139; 546/141
[58] Field of Search ............... 546/18, 101, 110, 546/114, 115, 116, 139, 141; 514/278, 290, 301, 302, 307, 309

[56] References Cited

U.S. PATENT DOCUMENTS

| Re. 35,112 | 12/1995 | Carney et al. | 514/400 |
|---|---|---|---|
| 3,044,930 | 7/1962 | Goodhue et al. | 167/46 |
| 3,796,715 | 3/1974 | Leimgruber et al. | 260/289 |
| 3,947,451 | 3/1976 | Jonsson et al. | 260/281 |
| 4,117,144 | 9/1978 | Jonsson et al. | 424/274 |
| 4,123,543 | 10/1978 | Jonsson et al. | 424/274 |
| 5,292,746 | 3/1994 | Carr et al. | 514/278 |
| 5,397,789 | 3/1995 | Carr et al. | 514/309 |
| 5,405,874 | 4/1995 | Carney et al. | 514/619 |
| 5,405,967 | 4/1995 | Janzen et al. | 548/542 |
| 5,455,272 | 10/1995 | Jansen et al. | 514/579 |
| 5,472,983 | 12/1995 | Flitter et al. | 514/599 |
| 5,475,032 | 12/1995 | Carney | 514/576 |
| 5,488,145 | 1/1996 | Carney | 562/62 |
| 5,527,828 | 6/1996 | Janzen et al. | 514/579 |
| 5,532,277 | 7/1996 | Janzen et al. | 514/579 |

FOREIGN PATENT DOCUMENTS

| 60532027 | 3/1993 | European Pat. Off. |
| 9105552 | 5/1991 | WIPO |
| 9222290 | 12/1992 | WIPO |
| 9511227 | 4/1995 | WIPO |
| 9511908 | 5/1995 | WIPO |

OTHER PUBLICATIONS

Role of oxygen free radicals in carcinogenesis and brain ischemia, FASEB Journal, vol. 4, pp. 2587–2599 (1990).
Use of Spin Traps in Intact Animals Undergoing Myocardial Ischemia/Reperfusion: A New Approach to Assessing the Role of Oxygen Radicals in Myocardial "Stunning", Free Rad. Res. Comms., vol. 9 No. 3–6, pp. 169–180, 1990.

Oxidative damage to brain proteins, loss of glutamine synthetase activity, and production of free radicals during ischemia/reperfusion–induced injury to gerbil brain, Proc. Natl. Acad. Sci. USA vol. 87, pp. 5144–5147 Jul. 1990, Neurobiology.
Protection from cerebral ischemic injury in gerbils with the spin trap agent N–tert–butyl–a–phenylnitrone (PBN) Neuroscience Letters, 116 (1990) 315–319.
Seeger, et al., "Chem. Ber.", vol. 103, 1970, pp. 1674–1691.
Thomae, "ChemicaL Abstracts," vol. 74, 1971, Col 141572c.
Kobor, "Chemical Abstracts," vol. 77, 1972, Col. 151841r.
Jonsson, et al., "Chemical Abstracts," vol. 78, 1973, Col. 159460g.
Patent Abstracts of Japan vol. 12, No. 283 (C–518)(3130) Aug. 3, 1988 & JP–A–63 063 851 (Univ. Osaka) Mar. 22, 1988.
Interleukin–1 and Interleukin–1 Antagonism, Blood, vol. 77, No. 8 (Apr. 15), 1991: pp. 1627–1652, Charles A. Dinarello.
An Unanesthetized–Gerbil Model of Cerebral Ischemia–induced Behavioral Changes, Journal of Pharmacological Methods 14, 137–146 (1985) Chandler, et al.
A Modified Bischler–Napieralski Procedure for the Synthesis of 3–Aryl–3,4–dihydroisoquinolines, J. Org. Chem. 1991, 56, 6034–6038, Larsen et al.
Reversal of age–related increase in brain protein oxidation, decrease in enzyme activity and loss in temporal and spatial memory by chronic administration of the spin–trapping compound N–tert–butyl–α–phenylnitrone, Proc. Natl. Acad. Sci. USA vol. 88, pp. 3633–3636, May 1991 Neurobiology, Carney et al.
Tungstate–Catalyzed of Secondary Amines to Nitrones. α–Substitution of Secondary Amines via Nitrones; J. Org. Chem. 1990, 55, 1736–1744.
Baggiolini, M. et al, Chemical Abstracts vol. 111, No. 25 Abstract 230.179e, p. 565, Dec. 18, 1989.
Dinarello, et al, Chemical Abstracts vol. 105, No. 21, Abstract 189195t, p. 591, Nov. 24, 1986.
Golubev et al. Chemical Abstracts, vol. 77, No. 16, Abstract No. 114, 156C, Oct. 16, 1972, pp. 428–419.
Maxwell, Simon R.J., *Drugs,* 49 (3) 1995, pp. 345–361.
Thomas, Craug E. et al., *Journal of Biological Chemistry,* vol. 269, No. 45, Nov. 11, 1994, pp. 28055–28061.
Thomas, Craug E. et al., *Journal of Biological Chemistry,* vol. 271, No. 6, 9 Feb. 9, 1996, pp. 3097–2104.

*Primary Examiner*—Richard L. Haymond
*Assistant Examiner*—Brenda Coleman
*Attorney, Agent, or Firm*—Stephen L. Nesbitt

[57] ABSTRACT

The present invention is directed to novel cyclic nitrones and their use in the prevention of oxidation tissue damage by free radicals, their use in the treatment of a number of disease states in which radicals either damage or destroy tissues via oxidation, and pharmaceutical compositions containing these cyclic nitrones.

16 Claims, No Drawings

CYCLIC NITRONES

This is a continuation of application Ser. No. 08/700,588, filed Aug. 16, 1996, abandoned, which claims the benefit of U.S. Provisional Application No. 60/003,551, filed Sep. 11, 1995: which is herein incorporated by reference.

The present invention is directed to cyclic nitrones, their use in the prevention of oxidative tissue damage by free radicals, their use in the treatment of a number of disease states in which radicals either damage or destroy tissues via oxidation, and pharmaceutical compositions containing these cyclic nitrones.

BACKGROUND OF THE INVENTION

Molecules containing an unpaired electron are referred to as free radicals. Free radicals are extremely reactive. Partial reduction of oxygen by mammalian biological systems produces the free radicals, superoxide and hydroxyl. The two electron reduction product of oxygen, hydrogen peroxide, is also produced but contains no unpaired electrons. However, it is usually a precursor to the hydroxyl radical which is the most reactive of the three. The hydroxyl free radical will react with almost any biomolecule. Examples of such biomolecules include nucleic acids, lipids, and proteins. The hydroxyl radical will oxidize the biomolecule by either extracting a hydrogen atom from the biomolecule or by adding directly to the biomolecule itself. This oxidation by the hydroxyl free radical transforms the biomolecule into a radical which will readily react with molecular oxygen, thereby forming what is referred to as a peroxyl free radical. The resulting peroxyl radical will react with another biomolecule producing a free radical, which will also be transformed into another peroxyl radical as described above. The initial presence of the oxygen free radical initiates a chain reaction in which a number of biomolecules in the organism are oxidized. By oxidizing lipids, these free radicals can affect cell membranes, their permeability, ion channels, cell function, etc. By oxidizing proteins, they can alter enzymes, muscular function, nerves, etc. By oxidizing nucleic acids, they can affect DNA, RNA, and their expression products.

Recent research has indicated that excessive levels of these oxygen free radicals are associated with the tissue damage which occurs in a number of disease states such as stroke, myocardial infarction, senile dementia, shock, etc. Stroke and septic shock in particular are disease states in which radical-induced tissue damage is prevalent. Recent research has also shown that spin trapping agents may be utilized to terminate the reaction cascade described above, thereby preventing or minimizing any tissue damage. Oxygen free radicals and carbon centered radicals will react more readily with the spin trapping agent than with a biomolecule. The reaction with the spin trapping agent will result in the formation of a stable radical adduct and thus will terminate the chain reaction that is typically associated with oxygen radicals. Most tissue damage results from the chain reaction that is initiated by the oxygen radical rather than by the oxygen radical itself. The mechanism of action by which oxygen radicals cause tissue damage, as well as the use of spin trapping agents to prevent this damage, is described more fully by Floyd, FASEB Journal, Vol. 4, page 2588 (1990).

Nitrones 3,4-dihydro-3,3-dimethylisoquinoline N-oxide (A) and spiro [cyclohexane-1,3']3,4-dihydroisoquinoline N-oxide (B)(FIG. 1) are cyclic analogs of the known radical scavenger PBN, which had previously been developed. Embedding the nitrone moiety in a cyclic system should give an essentially planar molecule in which good orbital overlap exists between the nitrone double bond and the aromatic ring. Molecular modelling studies indeed suggest that in the lowest energy conformation of A, the nitrone double bond is coplanar with the aromatic ring, whereas the corresponding relationship with PBN is ca. 30° offset from coplanarity. These predictions have been supported by X-ray crystallography. This increased degree of conjugation, relative to PBN, was expected to make the nitrone function in the cyclic analogs more accessible to radicals, and result in more stable product radicals. Experimentally, both A and B are more potent inhibitors of lipid oxidation, and better hydroxyl radical traps, than PBN. See U.S. Pat. No. 5,397,789, issued Mar. 14, 1995, incorporated herein by reference.

FIG. 1

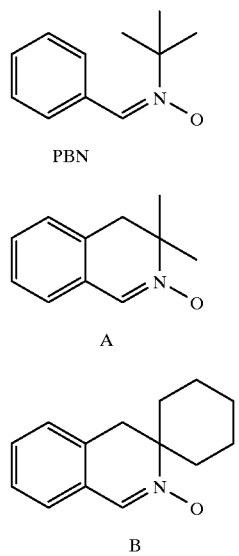

SUMMARY OF THE INVENTION

The compounds disclosed herein are cyclic nitrones of the formula:

FORMULA I

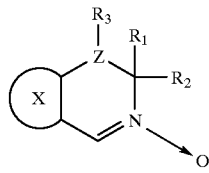

in which $R_1$ and $R_2$ are each independently represented by a $C_{1-3}$ alkyl or $R_1$ and $R_2$ together form a $C_{5-6}$ alkylene ring or a ring of the structure:

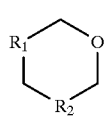

wherein $R_1$ and $R_2$ are each $CH_2$;

Z represents (CH$_x$)n, wherein x and n are each independently 0 or an integer from 1–2; R$_3$ is represented by a substituent selected from the group consisting of hydrogen, C$_{1-4}$ alkyl,

O;
∥ and the ring represented by X is a substituent selected from the group consisting of:

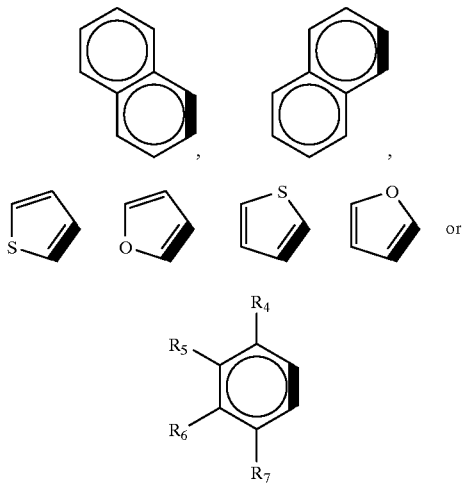

wherein the area of dark shading represents the side of attachment to the nitrone ring, R$_4$, R$_5$, R$_6$ and R$_7$ are independently selected from the group consisting of hydrogen, C$_1$–C$_3$ alkyl, OH or C$_{1-3}$ alkoxy, and the pharmaceutically acceptable salts thereof with the proviso that when R$_1$ and R$_2$ together form a C$_{5-6}$ alkylene ring and n is 1, then R$_3$ cannot be hydrogen.

As used in this application:
a) the term "C$_{1-3}$ alkyl" refers to a branched or straight chain alkyl group containing from 1–3 carbon atoms, such as methyl, ethyl, n-propyl, isopropyl, etc.;
b) the term "C$_{1-4}$ alkyl" refers to a branched or straight chain alkyl group containing from 1–4 carbon atoms, such as methyl, ethyl, n-propyl, isopropyl, n-butyl, isobutyl, etc.;
c) the term "C$_{1-3}$ alkoxy" refers to a straight or branched alkoxy group containing from 1–3 carbon atoms, such as methoxy, ethoxy, n-propoxy, isopropoxy, n-butoxy, isobutoxy, etc.;
d) the term "C$_{5-6}$ alkylene ring" refers to the closed structures:

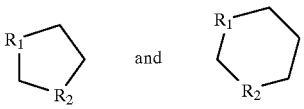

respectively, wherein R$_1$ and R$_2$ are each CH$_2$.

DETAILED DESCRIPTION OF THE INVENTION

Three general methods are used to make the cyclic nitrones. The "formamide route" is used whenever possible. The "isocyanate route" is used when the "formamide route" fails due to acid sensitivity of substrates or reaction intermediates. The "nitroaldehyde" route is used to prepare the major metabolite of A and related compounds. These routes will be described in detail for representative examples.

The Formamide Route

The "formamide route" is illustrated below for the synthesis of the naphthalene compounds 9 and 10 (see Scheme 1). Grignard addition to esters 1 and 2 provides tertiary alcohols 3 and 4 in good yield. Ritter reaction on these substrates with sodium cyanide affords the corresponding formamides 5 and 6. Reaction of the formamides with oxalyl chloride, followed by cyclization with FeCl$_3$ and acid hydrolysis (to cleave the oxalate residue), provides the cyclic imines 7 and 8 (see Larsen, R. D.; Reamer, R. A.; Corley, E. G.; Davis, P.; Grabowski, E. J. J.; Reider, P. J.; Shinkai, I., *J. Org. Chem.* 1991, 56, 6034). A single regioisomer is obtained in each case. Oxidation to the nitrones 9 and 10 proceeds more rapidly and efficiently when the imines are first reduced to the corresponding amines with sodium borohydride. It will be understood in the following schemes, examples and text that the sodium tungstate (Na$_2$WO$_4$) catalyst is the dihydrate form, i.e. Na$_2$WO$_4$.2H$_2$O.

Scheme 1

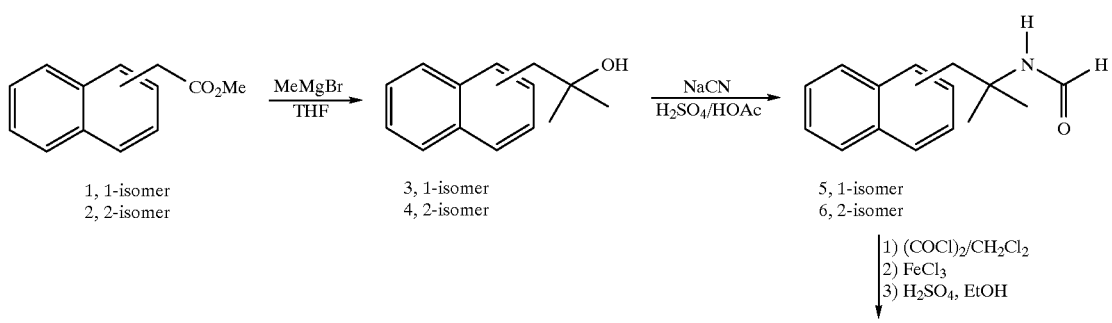

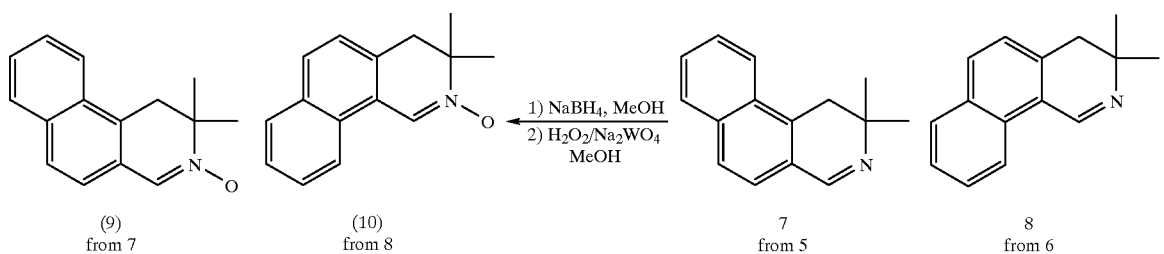

| (9) | (10) | 7 | 8 |
| from 7 | from 8 | from 5 | from 6 |

The compounds shown in FIG. 2 can all be prepared by this formamide route, or variations thereof.

FIG. 2

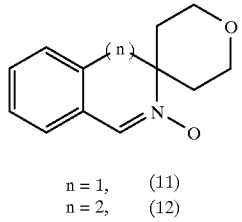

n = 1, (11)
n = 2, (12)

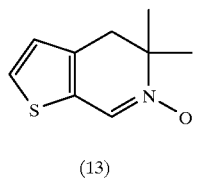

(13)

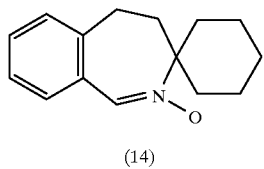

(14)

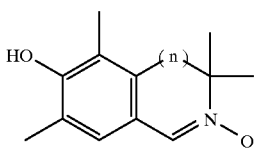

n = 1, (15)
n = 2, (16)

The synthesis of the spiropyran analogs 11) and 12 proceeds similarly to the naphthalene compounds except the intermediate tertiary alcohols 17 and 18 are obtained by addition of benzyl- or phenethylmagnesium halide to the requisite pyranone (Scheme 2).

Scheme 2

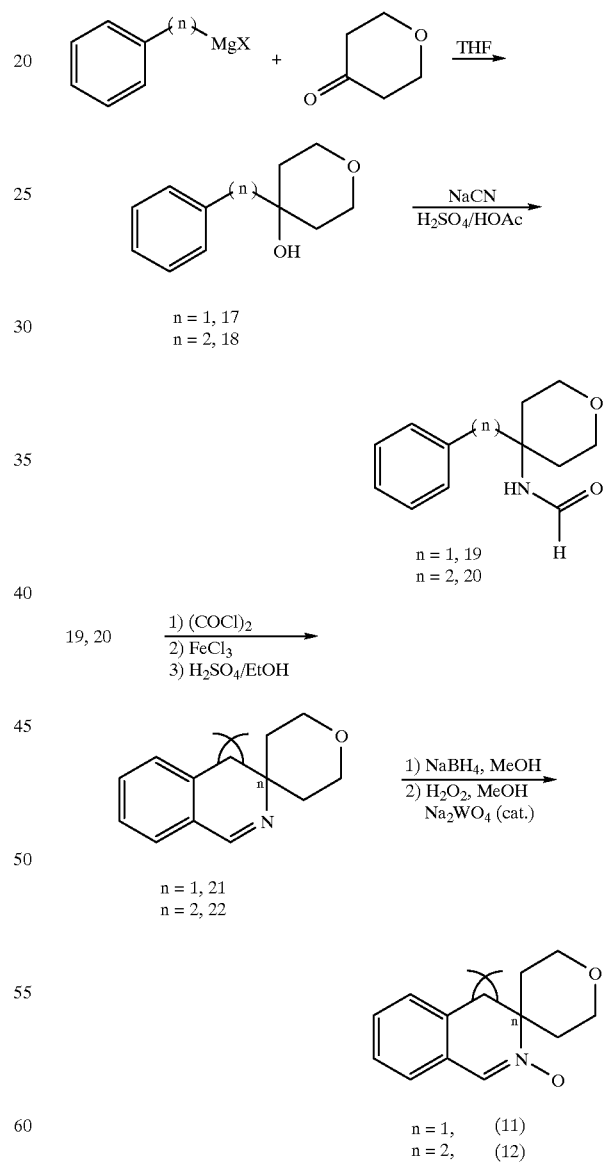

n = 1, 17
n = 2, 18 n = 1, 19
n = 2, 20 n = 1, 21
n = 2, 22 n = 1, (11)
n = 2, (12)

The synthesis of the phenol analog, 15 is shown in Scheme 4. Tertiary alcohol 29 is readily obtained in -preparation for the Ritter reaction. After protection of the para position by bromination, latent methyl groups are placed ortho to the phenolic hydroxyl via a double Mannich reaction with an amine and aqueous formaldehyde.

Scheme 3

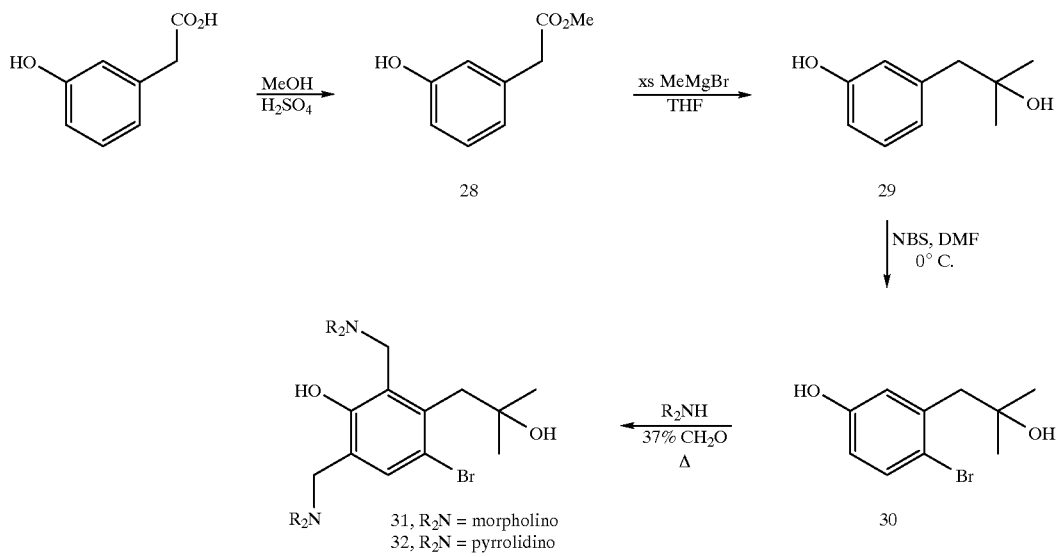

Treatment of 32 with p-methoxybenzylthiol affords the bis(sulfide) 37 in good yield (see Popplesdorf, F.; Holt, S., *J. Chem. Soc.* 1954, 1124). Treatment of 37 with Raney nickel (RaNi) then provides 33.

Scheme 4

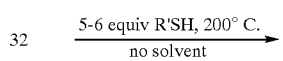

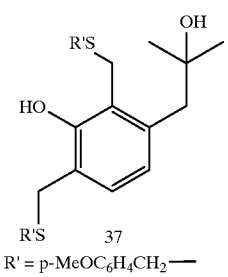

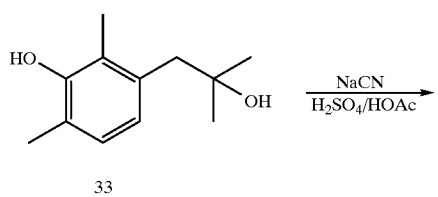

-continued

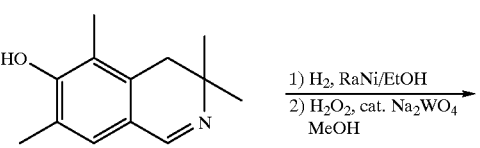

38

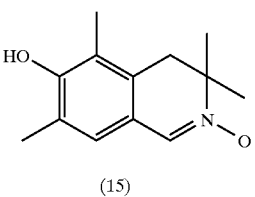

(15)

The Ritter reaction of 33 with NaCN gives the cyclized imine 38 directly (Scheme 4). Imine 38 is then converted into 15, as shown in scheme 4.

The chemistry shown in Schemes 3 and 4 can be used to prepare the corresponding 7-membered ring analog 16. The required ester intermediate 42 in this case is synthesized from the commercially available acid 40 as shown in Scheme 5.

Scheme 5

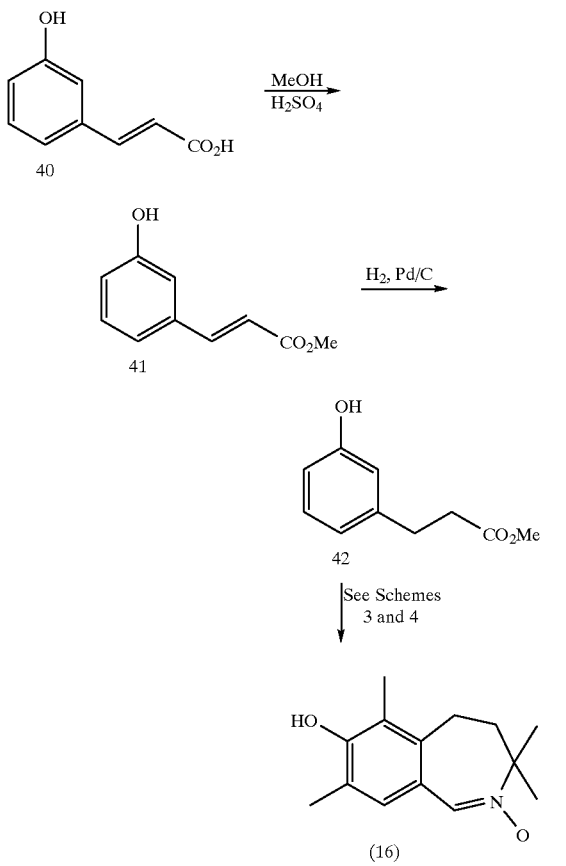

Scheme 6

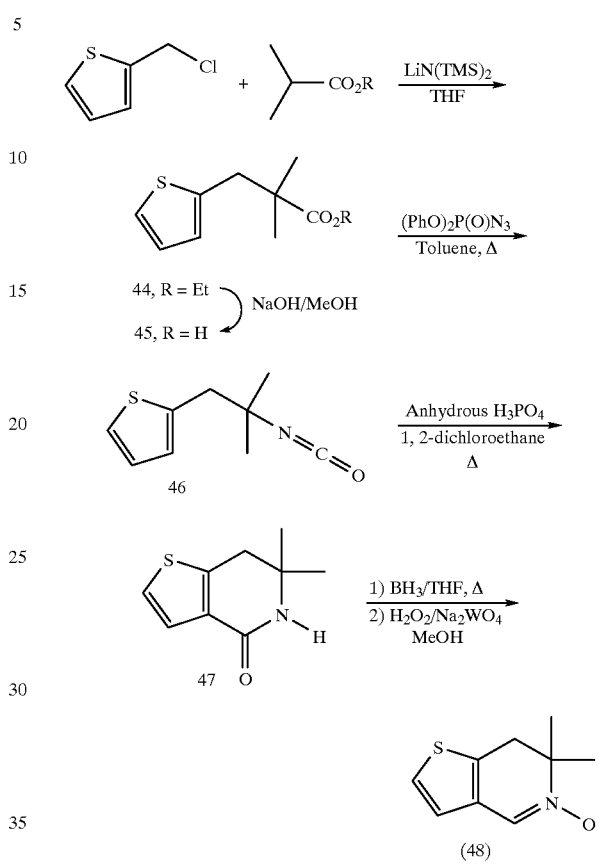

The Isocyanate Route

The isocyanate route is shown in Scheme 6. Alkylation of ethyl isobutyrate with chloromethyl thiophene, and subsequent hydrolysis of the ester (44), gives the Curtius rearrangement substrate 45. The isocyanate 46 is formed smoothly, and is easily isolated after an aqueous work-up. Compound 46 cyclizes readily upon treatment with anhydrous $H_3PO_4$ in hot dichloroethane (DCE). Umezawa, B.; Hoshino, O.; Sawaki, S.; Mori, K. *Chem. Pharm. Bull.* 1980, 28, 1003. The resulting lactam 47 is reduced to the corresponding amine with borane, whereupon standard oxidation gives 48.

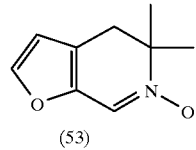

(53)

An analogous pathway is used to prepare the furan analog 53. $BF_3$ etherate proving to be a better cyclization catalyst in this case.

Isocyanate 56 is easily prepared in high overall yield, and on large scale, as shown (Scheme 7).

Scheme 7

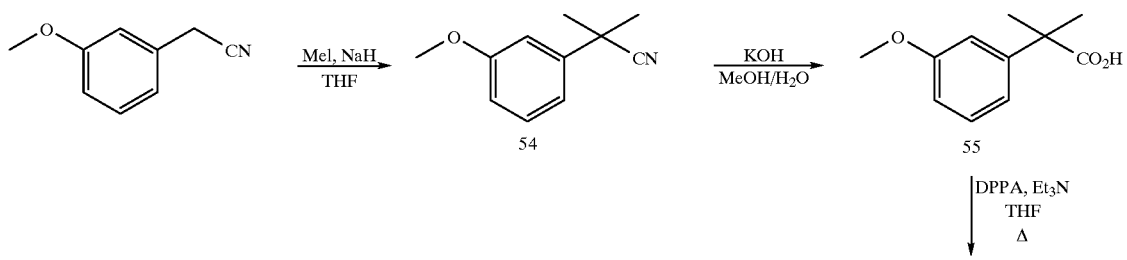

-continued

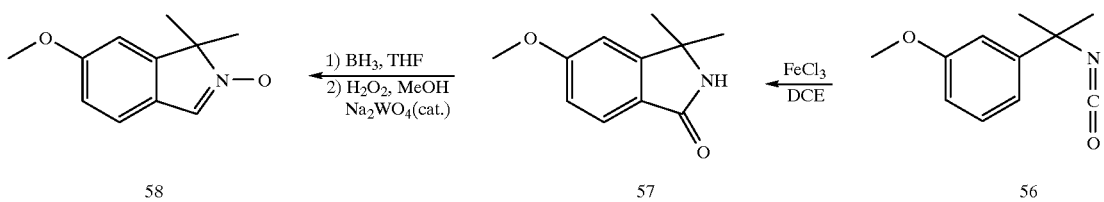

Treatment of 56 with FeCl₃ in DCE affords 57 and a regioisomeric lactam 61 (7-methoxy-3,3-dimethyl-2,3-dihydroisoindol-1-one)[not shown](3:1 ratio) in 55% yield.

The synthesis can be completed for each lactam 57 (and 61 not shown) as shown for the major isomer 57 (Scheme 7). In an analogous manner the compound 4-methoxy-1,1-dimethyl-1H-isoindole N-oxide (see example 14) can be made starting with lactam 61.

Scheme 8

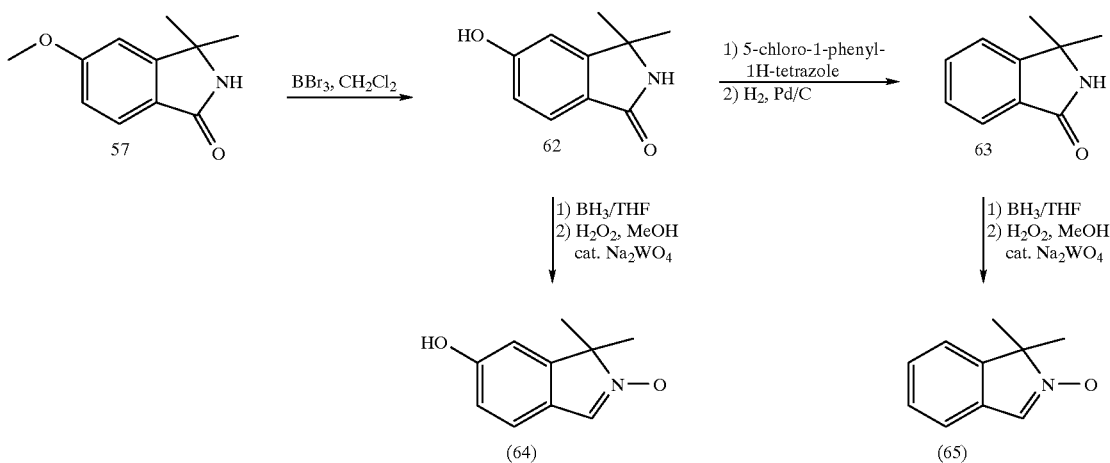

In order to prepare the 5-membered ring nitrone lacking the methoxy group 65, lactam 57 is subjected to the sequence of reactions shown in Scheme 8. *Deoxygenation of Phenols*, Musliner, W. J.; Gates, Jr. J. W.; *J. Am. Chem. Soc.* 1966, 88, 4271. A portion of the intermediate hydroxy lactam can be converted into 64.

Compound A (see FIG. 1, supra) causes sedation when administered in high doses in rats. Indeed, from the onset, a primary goal has been to find a potent antioxidant which lacks this side effect observed with compound A. In this regard, the following observations were of special interest. The sedative effect peaks and declines rapidly, whereas the in vivo activity persists for a considerably longer period of time. The decline in sedation coincides with the appearance of a major metabolite of A, and this led to the speculation that the metabolite retains the antioxidant activity of the parent, but does not cause sedation. In order to investigate this possibility, the major metabolite C and a minor, possibly secondary, metabolite (Metabolite 2) were isolated from an in vivo experiment, purified by HPLC, and assigned the structures shown below (FIG. 3).

Figure 3

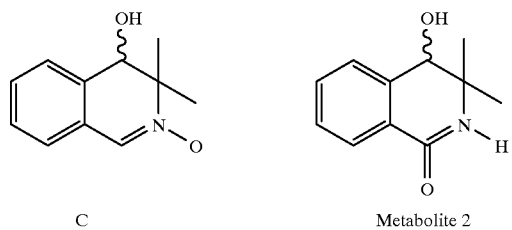

Compound C is much more abundant in vivo than Metabolite 2, and retains the nitrone functionality, and is therefore more likely to be the putative non-sedating antioxidant.

The target molecule, C, is prepared in three steps from commercially available starting materials: 2-nitropropane and orthophthalaldehyde (Scheme 9). Reaction of these two substrates in the presence of freshly prepared sodium methoxide in methanol, followed by acidification, gives rise to the cyclic acetals 71 (a ca. 1:1 mixture of cis and trans isomers) in 70% yield after chromatography. Marquard, F-H.; Edwards, S. *J. Org. Chem.* 1972, 37, 1861. Alternatively, the crude product (quantitative crude yield, 86% purity by gas chromatography (GC) can be carried on to the next step without purification (see below).

Scheme 9

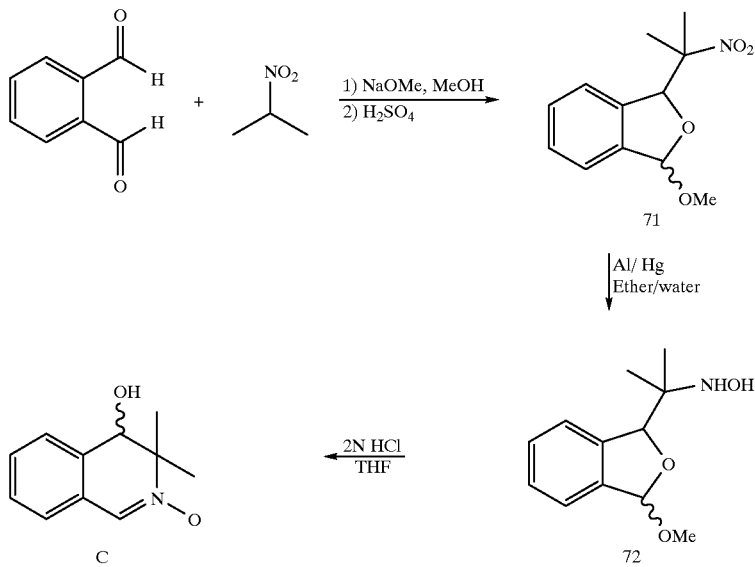

The nitro acetal 71 is reduced to hydroxylamine 72 by treatment with aluminum amalgam in ether/water according to a literature procedure. Calder, A; Forrester, A. R.; Hepburn, S. P. *Org. Syn. Coll. Vol. VI.* 1988, 803. The yield of purified 72 from orthophthalaldehyde is ca. 45% whether or not the intermediate nitroacetal 71 is purified.

Finally, treatment of hydroxylamino acetal 72 with aqueous HCl in THF provides C, cleanly and rapidly. The crude product can be purified to homogeneity by a single crystallization from cyclohexane/EtOAc or hexane/ dichloromethane to give C in 67% yield. The yield in this reaction is limited by the relatively high water solubility of the product.

Finally, several derivatives and analogs of the C were prepared. Ketone analogs are especially interesting since they would be less polar than the alcohols, have electron withdrawing groups in conjugation with the nitrones, and have no chiral centers. Conversion of C into the ketone 77 and the acetate 76 derivatives is easily accomplished Spirocyclohexyl and spirocyclopentyl analogs of C and MDL 77 (FIG. 4) are prepared in exactly the same way, but starting with nitrocyclohexane and nitrocyclopentane, respectively, in place of nitropropane.

FIG. 4

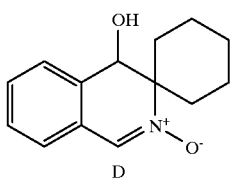

Scheme 10

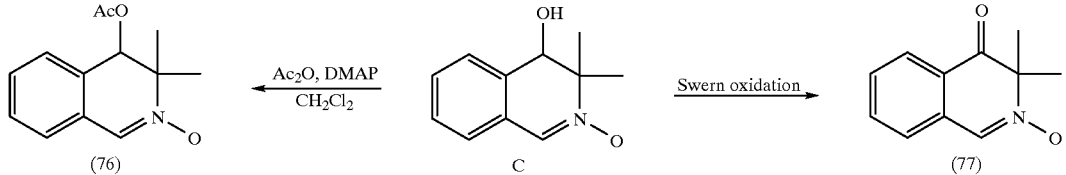

-continued

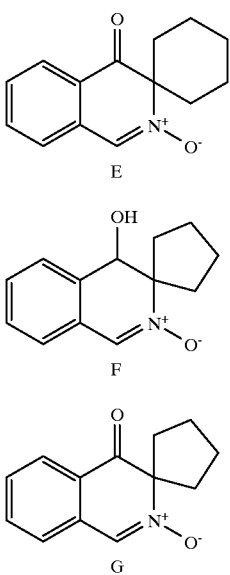

Some of the compounds of the invention contain an asymmetric center and will exist as optical isomers. Any reference in this application to one of the compounds represented in FIG. 3 is meant to encompass either a specific optical isomer or a mixture of optical isomers. The specific optical isomers can be separated and recovered by techniques known in the art such as chromatography on chiral stationary phases, or enzymatic hydrolysis using stereoselective esterases as is known in the art.

COMPOUND EVALUATION

Oxidation of cellular macromolecules, including lipids and DNA, has been implicated in the etiology of numerous disease states. In the central nervous system (CNS), both stroke and neurotrauma have been proposed to initiate a sequelae of oxidative events which ultimately lead to neuronal cell death Kontos, H. A. (1989) Chem.-Biol. Interactions 72, 229–255. Brain neuronal membranes contain a high percentage of polyunsaturated fatty acids and an abundance of iron and ascorbic acid. Collectively, these properties yield neural tissue highly vulnerable to oxygen radical formation and lipid peroxidation. Iron and ascorbic acid can participate in the formation of radicals such as the hydroxyl radical (.OH) which are capable of initiating lipid peroxidation. Cellular responses to the ischemic or hypoxic environment which arise following the occlusion of an artery or following traumatic insult favor the generation of oxygen radicals. For example, aberrant mitochondrial electron transport due to lack of oxygen leads to a buildup in reducing equivalents which can partially reduce dioxygen to produce superoxide ($O_2^-$) and hydrogen peroxide ($H_2O_2$) upon reperfusion. Catecholamine accumulation, the conversion of xanthine dehydrogenase to its oxidase form, the release of arachidonic acid from phospholipids, and the attraction of neutrophils to ischemic tissue are other reported changes which all favor a highly oxidizing environment.

Animal models of global and focal ischemia have provided evidence for the production of oxygen radicals and the occurrence of lipid peroxidation. Increases in lipid-derived conjugated dienes and decreases in the protective antioxidant α-tocopherol (vitamin E) have been observed in rats subjected to brain ischemia-reperfusion. Hall, E. D. and Braughler, J. M. (1989) J. Free Rad. Biol. Med. 6, 303–313. In agreement, brain tissue from animals rendered deficient in vitamin E was more susceptible to ischemia-induced damage while vitamin E supplementation had some protective effect. Yoshida, S., Busto, R., Watson, B. D., Santiso, M., and Ginsberg, M. (1985) J. Neurochem. 44, 1593–1601. Pentane evolved from lipid peroxidation has been found in the expired breath of gerbils subjected to global ischemia and reperfusion, which also supports the contention that neuronal lipid oxidation occurs under these conditions. Mickel, H. S., Vaishnav, S. Y. N., Kempski, O., von Lubitz, D., Weiss, J. F., and Feuerstein, G. (1987) Stroke 18, 426–430.

Oxidative events following CNS ischemia-reperfusion are not limited to lipids. In gerbils, global ischemia resulted in oxidation-induced protein carbonyl formation and in loss of activity of glutamine synthetase, an enzyme susceptible to oxidative inactivation. Oliver, C. N., Starke-Reed, P. E., Stadtman, E. R., Liu, G. J., Carney, J. M., and Floyd, R. A. (1990) Proc. Natl. Acad. Sci USA 87, 5144–5147.

Subjecting brain cortical slices to hypoxia and reoxygenation or injection of iron into CNS tissue leads to a loss of $Na^+$, $K^+$-ATPase activity which may reflect direct protein oxidation and/or perturbation of the associated membrane bilayer. Taylor, M. D., Mellert, T. K., Parmentier, J. L., and Eddy, L. J. (1985) Brain Res. 346, 268–273; Anderson, D. K. and Means, E. D. (1983) Neurochem. Pathol. 1, 249–264.

While the evidence implicating oxygen radical formation as a cause of neuronal injury remains largely circumstantial, various antioxidant therapies have been tested for their ability to prevent or minimize loss of cell viability. As mentioned above, prior administration of vitamin E has been shown to provide partial protection. Limited success has been achieved with various forms of superoxide dismutase (SOD) and transgenic animals overexpressing SOD are more resistant to ischemia-induced injury. Kinouchi, H., Epstein, C. J., Mizui, T., Carlson, E., Chen, S. F., and Chan, P. H. (1991) Proc. Natl. Acad. Sci. USA 88, 11158–11162. Recently, investigators have reported that the nitrone spin trap alpha-phenyl-tert-butyl nitrone (PBN) can significantly ameliorate neuronal cell loss and neurologic deficits induced by stroke in a gerbil model. Phillis, J. W., and Clough-Helfman, C. (1990) Med. Sci. Res. 18, 403–404. Yue, T. -L., Gu, J. -L., Lysko, P. G., Cheng, H. -Y., Barone, F. C., and Feuerstein, G. (1992) Brain Res. 574, 193–197. Furthermore, PBN was shown by electron spin resonance (ESR) spectroscopy to trap lipid-derived radicals in cortical tissue of these animals.

Nitrone spin traps such as PBN have been utilized for a number of years to allow the trapping of short lived reactive radicals such as .OH. The resultant nitroxide is a more stable radical and can be detected by electron spin resonance spectroscopy. More recently, investigators have demonstrated that nitrones like PBN can inhibit the oxidation of lipids including low density lipoproteins and proteins such as glutamate synthetase. Thomas, C. E., Ku, G., and Kalyanaraman, B. (1994) J. Lipid Res. 35, 610–619; Thomas, C. E., Ohlweiler, D. F., and Kalyanaraman, B. (1994) J. Biol. Chem. 269, 28055–28061(use of antioxidants in the treatment of atherosclerosis); Carney, J. M., StarkeReed, P. E., Oliver, C. N., Landrum, R. W., Cheng, M. S., Wu, J. F., and Floyd, R. A.(1991) Proc. Natl. Acad. Sci. USA 88, 3633–3636.

Another pathophysiologic situation wherein a role for oxygen radicals has been oft proposed is septic shock, which can be characterized as a systemic response to a serious infection. The resultant activation of inflammatory cells such as leukocytes is expected to result in the formation of $O_2^-$ and $H_2O_2$. Indeed, evidence of free radicals and free radical mediated tissue damage has been reported in animal models of endotoxic shock and in humans with septic shock. Takeda, K., Shimada, Y., Okada, T., Amono, M., Sakai, T., and Yoshiya, I. (1986) *Crit. Care Med.* 14, 719–723. Novelli, G. P., Angiolini, P., Livi, P., and Paternostro, E. (1989) *Resuscitation* 18, 195–205. Biasi, F., Chiarpotto, E., Lanfranco, G., Capra, A., Zummo, U., Chiappino, I., Scavazza, A., Albano, E., and Poli, G. (1994) *Free Rad. Biol. Med.* 17, 225–233. Interestingly, PBN has been demonstrated to reduce endotoxin associated mortality in rats. Hamburger, S. A., and McCay, P. B. (1989) *Circ. Shock* 29, 329–334. Thus, the use of spin traps like PBN may provide new therapeutics for the treatment of various disease states. See "Prospects for the Use of Antioxidant Therapies", *Drugs* 49(3) 1995, 345–361. In addition, the ability of the nitrones to trap and stabilize radicals may provide a potential means to identify radicals which are generated in vivo. For these reasons, we have synthesized and evaluated a novel series of nitrone spin traps for in vitro radical trapping activity.

MATERIALS AND METHODS

Cyclic nitrones were prepared as described above.
Chemicals

2-Deoxy-D-ribose, $FeCl_2$, $FeCl_3$, disodium EDTA, 30% $H_2O_2$, ascorbic acid, thiobarbituric acid (TBA), 100% trichloroacetic acid (TCA) solution, butylated hydroxytoluene (BHT), NADPH, p-nitrosodimethylaniline (p-NDA), reduced glutathione (GSH), diethylenetriaminepentaacetic anhydride (DETAPAC), xanthine, xanthine oxidase (from buttermilk), N-methyl-D-glucamine, HEPES, 3-(4,5-dimethylthiazol-2yl)-2,5-diphenyl tetrazolium bromide (MTT), Cu,Zn-superoxide dismutase (SOD) and 1,1,3,3-tetraethoxypropane were purchased from Sigma Chemical Co. Soybean phosphatidylcholine was a product of Avanti Polar Lipids while PBN and β-cyclodextrins were purchased from Aldrich. Cell culture supplies were obtained from Gibco or Sigma. All other chemicals were of the highest grade available.

Radical trapping in vitro by the cyclic nitrones was evaluated by: 1) examining the ability of the nitrones to inhibit oxidation of soybean phosphatidylcholine liposomes; 2) assessing .OH trapping using p-nitrosodimethylaniline or 2-deoxyribose and 3) ESR spin trapping for .OH and $O_2^-$.

1. Inhibition of lipid peroxidation

For determination of the ability to inhibit lipid peroxidation, liposomes were prepared from soybean phosphatidylcholine by ethanol injection. An aliquot of phosphatidylcholine was dried in a small glass vial under $N_2$. The lipid was resolubilized in ethanol at a volume of 10 ml per ml of liposomes. Typically, 8 ml volumes of liposomes were prepared per tube and then all preparations were combined to provide a homogenous mixture for the assay. The ethanol containing the lipid was taken up in a Hamilton syringe and injected into the appropriate volume of 50 mM NaCl/10 mM Tris, pH 7.0 at 37° C. with mixing to achieve a final lipid concentration of 0.563 mM.

The liposomes were added to 25 ml beakers in a Dubnoff metabolic shaker at 37° C. To the liposomes were added the test compound (in ethanol or buffer), histidine-$FeCl_3$ 250:50 mM final), $FeCl_2$ (50 mM final, prepared in $N_2$ purged water) and sufficient buffer to achieve a final lipid concentration of 0.5 mM. Oxidations were initiated by the addition of $Fe^{2+}$ and carried out under an air atmosphere with shaking. One ml aliquots were removed at 0,2,4,6,8,10,12 and 15 min and added to 2 ml of 0.67% thiobarbituric acid : 10% trichloroacetic acid (2:1) in 0.25 N HCl containing 0.05 ml of 2% BHT to terminate oxidation. Thomas, C. E., McLean, L. R., Parker, R. A., and Ohlweiler, D. F. (1992) *Lipids* 27, 543–550.

The samples were heated at 100° C. for 20 min in 13 x 100 mm borosilicate glass tubes covered with marbles to prevent evaporation. After cooling, the tubes were centrifuged at 3,000 rpm for 10 min and the absorbance of the resultant supernatant read at 532 nm–580 nm. Quantitation of thiobarbituric acid reactive substances (TBARS) was determined by comparison to a standard curve of malondialdehyde equivalents generated by acid catalyzed hydrolysis of 1,1,3,3-tetraethoxypropane. The $IC_{50}$ was determined using the 15 min time point with the computer program GraphPad INPLOT 4. This program uses a nonlinear regression with sigmoidal curve on a semilogarithmic scale. These results are tabulated in Table I.

2. Assessment as .OH Traps

A. Inhibition of the bleaching of p-NDA

Cyclic nitrones were evaluated for .OH trapping activity by a variety of tests. The primary assay was dependent upon the ability of the compounds to inhibit the .OH-dependent bleaching of p-NDA. Bors, W., Michel, C., and Saran, M. (1979) *J. Biochem.* 95, 621–627. The p-NDA was prepared at 1 mM in 50 mM NaCl, pH 7.0. The hydroxyl radical was generated using Fenton chemistry ($Fe^{2+}/H_2O_2$). $FeCl_2$ is dissolved in $N_2$ purged, double distilled $H_2O_2$to a final concentration of 2.5 mM. $H_2O_2$ was prepared from a 30% stock solution (8.8 M) at 1.25 mM in the buffer. Test compounds were solubilized in buffer or ethanol at a concentration of 1 M or 5 M, depending upon solubility.

Assay mixtures in glass cuvettes contained solutions of 0.02 ml of $H_2O_2$, 0.02 ml of test compound, 0.10 ml of p-NDA and 50 mM NaCl, pH 7.0 to a final volume of 0.98 ml. The oxidation was initiated by the addition of 0.02 ml of $Fe^{2+}$ and the bleaching of p-NDA was monitored as the loss in absorbance at 440 nm for 100 sec. To generate concentration curves, serial dilutions of the test compounds were made such that a constant volume of 0.02 ml was added to the reaction mixture. Ethanol itself is an .OH trap, thus controls contained an equal volume of ethanol for any test compound requiring this vehicle. The $IC_{50}$ values for the nitrones were determined by GraphPad InPlot 4 and represent the amount of spin trap required to inhibit the bleaching of p-NDA by 50%.

B. Inhibition of 2-deoxyribose degradation

In this assay, hydroxyl radicals are also generated by Fenton's reaction. Their subsequent reaction with 2-deoxyribose causes this sugar molecule to break down to products reactive with TBA which can be measured spectrophotometrically. The $Fe^{3+}$ used in this assay is reduced to $Fe^{2+}$ by ascorbic acid and EDTA is used as an iron chelator to prevent site-specific damage directly to the deoxyribose molecule by the iron.

Stock Solutions

The buffer used in the incubation assay was a modified 30 mM Sorenson's buffer containing 40 mM NaCl, pH 7.4. It was prepared with 19% 30 mM $Na_2HPO_4$ and 81% 30 mM $NaH_2PO_4$, with NaCl added to yield a concentration of 40 mM.

Stock solutions were prepared as follows:
1) 100 mM 2-deoxyribose=13.41 mg/ml buffer
2) 100 mM $H_2O_2$=50 μl 30% $H_2O_2$ solution+4.4 ml buffer
3) 10 mM EDTA/10 mM $Fe^{3+}$=3.72 mg disodium EDTA+ 2.70 mg $FeCl_3.6H_2O$/ml buffer 4) 10 mM ascorbic acid=1.761 mg/ml buffer
5) Radical scavengers to be assayed were prepared as stock solutions ranging from 5 to 100 mM in buffer, depending on their solubility. Organic solvents, such as methanol or ethanol, could not be used since even as small a volume as 5 ml of the solvent alone would substantially inhibit 2-deoxyribose degradation.
6) 0.378% TBA/15.2% TCA/0.014% BHT
   a) 16.7% TCA=20 ml 100% TCA solution+100 ml 0.125 N HCl
   b) 0.416% TBA=0.500 g TBA+120 ml 16.7% TCA solution (heated)
   c) 100 ml TBA/TCA solution+10 ml 0.15% BHT in ethanol
7) 1.0 mM malondialdehyde (MDA)=200 μl 4.4 mM MDA+0.880 ml 10% TCA
   a) 4.4 mM MDA=10 μl of 4.4 M 1,1,3,3-tetraethoxypropane+9.99 ml 10% TCA Standards MDA standards were prepared as follows:
1) 0.0 nmoles/ml=1.00 ml buffer
2) 10 nmoles/ml=10 μl 1.0 mM MDA+0.990 ml buffer
3) 25 nmoles/ml=25 μl 1.0 mM MDA+0.975 ml buffer
4) 50 nmoles/ml=50 μl 1.0 mM MDA+0.950 ml buffer Incubations Incubations were performed in 20 ml beakers in a shaking water bath set at 37° C. and exposed to ambient air. The following constituents were added in the order listed: 1) buffer to make final volume 5.0 ml (4.71 ml for control); 2) 5 μl to 4.5 ml radical scavenger of interest (final concentration range of 5 μM to 4 mM); 3) 140 μl 100 mM 2-deoxyribose (2.8 mM); 4) 50 μl 100 mM $H_2O_2$ (1.0 mM); 5) 50 μl 10 mM EDTA/10 mM $Fe^{3+}$ (100 mM); and 6) 50 μl 10 mM ascorbic acid (100 mM).

At the 0 and 15 min time points after the addition of the ascorbic acid, 1.0 ml aliquots of incubation media were pipetted to tubes containing 2.0 ml TBA/TCA/BHT solution. Standards were also added to tubes containing 2.0 ml TBA/TCA/BHT. After vortexing, the covered samples and standards were heated in a heating block at 100° C. for 20 min. The samples were cooled and centrifuged at 1500×g for 10 min. Absorbances were read at $A_{532}-A_{580}$. The radical scavenger concentration which inhibits TBARS formation by 50% ($IC_{50}$) was calculated using GraphPad INPLOT.

Determination of Rate Constant ($k_s$) for Reaction of Hydroxyl Radicals With Radical Scavengers When a hydroxyl radical scavenger is added to this reaction, a simple competition between the scavenger and the deoxyribose molecule takes place. From the method of Ching, T., Halnen, G. R. M. M., and Bast, A. (1993) *Chem-Biol Interactions* 86,119–127, the rate constant for the reaction of the scavenger with hydroxyl radical can be calculated with the equation:

$$1/A=1/A^* (1+k_s[S]/k_{DR}[D])$$

where
A=absorbance in presence of radical scavenger
[S]=radical scavenger concentration
A*=absorbance in absence of radical scavenger
$k_s$=rate constant for reaction of scavenger with hydroxyl radical
$k_{DR}$=rate constant for reaction of 2-deoxyribose with hydroxyl radical=$3.1 \times 10^9$ $M^{-1}$ $sec^{-1}$
[D]=2-deoxyribose concentration=2.8 mM If 1/A is plotted against [S], then $$slope=k_s/k_{DR}[D]A^*$$

$$k_s=slope \times k_{DR} \times [D] \times A^*$$

3. Protection of cerebellar granule cells against oxidative damage

The cyclic nitrones were tested for their ability to protect primary cultures of cerebellar granule cells against oxidative injury induced by treatment with $Fe^{2+}$. Cerebellar granule cell cultures were prepared from 8 day old rats as previously described. Levi, G., Aloisi, F., Ciotti, M. T., Thangnipon, W., Kingsbury, A., and Balazs, R. (1989) In: *A Dissection and Tissue Culture Manual of the Nervous System* (Shahar, A., de Vellis, J., Vernadakis, A., and Haber, B., eds.) Alan R. Liss, Inc. New York, N.Y., pp. 211–214. Briefly, 8–10 cerebella were removed and placed in a Krebs-Ringer bicarbonate medium supplemented with BSA and $MgSO_4$. Cerebella were finely chopped and digested with a trypsin/Krebs-Ringer solution. Cells were then dispersed by trituration in Krebs-Ringer containing DNase, $MgSO_4$ and trypsin inhibitor followed by plating at a density of $1 \times 10^6$ cells/well in poly-l-lysine coated plate in MEM/10% fetal bovine serum/KCl/glutamine/gentamicin. Media was replaced at 24 hours and cytosine arabinoside added. Experiments were conducted with cells 8–10 days in vitro.

For oxidation studies the media was removed and replaced with $Na^+$ free Locke's solution (154.6 mM N-methyl-D-glucamine, 5.6 mM KCl, 2.3 mM $CaCl_2$, 1 mM $MgCl_2$, 3.6 mM $NaHCO_3$, and 5 mM HEPES, pH 7.3) with the omission of glucose. The nitrones were added in either Locke's solution or in 20% β-cyclodextrins and allowed to incorporate into the cells for 30 min. At this time 20 μl of a 5 mM stock solution of ferrous chloride was added for a final concentration of 100 μM. After 45 min the media was removed and added to 1.5 ml of TBA/TCA (2:1) with 25 μl of 2% BHT and TBARS determined as described above. The absorbance of the control cells (no iron) was subtracted from the iron treated cells and this value taken as the denominator to determine the concentration of nitrone required to inhibit oxidation by 50%.

Fresh MEM media was added to the cells along with 100 μl of MTT. After 4 hrs, 1 ml of cold isopropanol/0.04 N HCl was added, the cells scraped, mixed well and transferred to 13×100 mm glass test tubes. The absorbance resulting from mitochondrial reduction of the MTT (570 nm minus 630 nm) was measured as an assessment of viability. The % cell death was determined by comparison to the absorbance of cells to which no iron was added. The difference between the iron-treated and control cells was taken as 100% and the concentration of nitrone to prevent the loss of MTT reduction capability(expressed in Table II as viability) by 50% was used as the $IC_{50}$.

The cyclic nitrones that were prepared are listed in Table I along with their $IC_{50}$ values for inhibition of lipid oxidation and hydroxyl radical trapping in vitro. MDL 101,002 is included for comparison.

TABLE I
| COMPOUND | Compound # | LIPID OX (IC$_{50}$) | OH RADICAL TRAPPING |
|---|---|---|---|
| 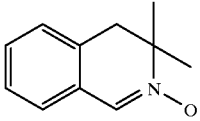 | A | 1.67 mM | 2.83 mM |
| 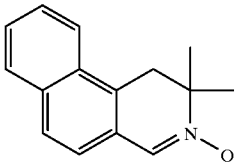 | 9 | 0.1 mM | not measured low solubility |
| 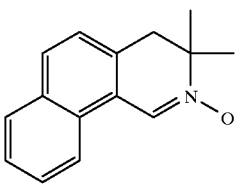 | 10 | 0.069 mM | not measured |
| 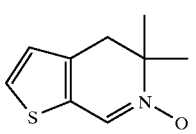 | 13 | 1.72 mM | 4.34 mM |
| 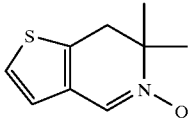 | 48 | 1.59 mM | 14.4 mM |
| 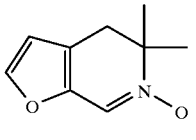 | 53 | 1.07 mM | no effect at 20 mM |
| 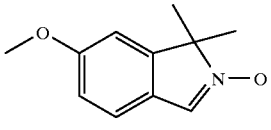 | 58 | 0.909 mM | not determined |
| 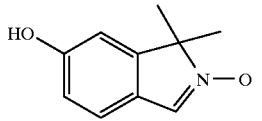 | 64 | 0.809 mM | not determined |
| 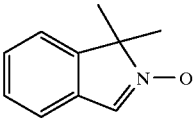 | 65 | 1.364 mM | not determined |
| see FIG. 4 | D | 0.539 mM | not determined |
| see FIG. 4 | E | 0.027 mM | not determined |
| see FIG. 4 | F | 1.04 mM | not determined |
| see FIG. 4 | G | 0.157 mM | not determined |

TABLE I-continued

| COMPOUND | Compound # | LIPID OX (IC$_{50}$) | OH RADICAL TRAPPING |
|---|---|---|---|
|  | see eg. 14 | 1.085 mM | not determined |

TABLE II

IC$_{50}$ Values for Inhibition of Fe$^{2+}$-Induced Damage to Cerebellar Granule Cells

| Compound | TBARS IC$_{50}$ ($\mu$M) | Viability IC$_{50}$ ($\mu$M) |
|---|---|---|
| PBN | 2600 | 2600 |
| A (R=H) | 307 | 292 |
| 10 (naphthyl) | 104 | 103 |
| 48 (sulfophenyl) | 2600 | 880 |
| 15 (dimethyl phehol) | 220 | 190 |
| C (metabolite) | 1900 | 1550 |
| 76 (acetate of metabolite) | 839 | 864 |
| D (spirohexyl hydroxy) | 520 | 588 |
| E (spirohexyl ketone) | 37 | 39 |
| F (spiropentyl hydroxy) | 771 | 817 |
| G (spiropentyl ketone) | 102 | 105 |
| 77 (ketone of metabolite) | 830 | 385 |

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically a protective amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of the invention can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The compounds of the invention may be administered in the amount of from 0.01 mg/kg to 500 mg/kg, depending on a variety of factors such as weight, age, sex, condition being treated,etc.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention applies.

As used in this application:
a) the term "patient" refers to warm blooded animals such as, for example, guinea pigs, mice, rats, gerbils, cats, rabbits, dogs, monkeys, chimpanzees, and humans;
b) the term "treat" refers to the ability of the compounds to either relieve, alleviate, or slow the progression of the patient's disease or any tissue damage associated with the disease;
c) the term "neurodegeneration" refers to a progressive death and disappearance of a population of nerve cells occurring in a manner characteristic of a particular disease state and leading to brain or other neuronal damage.
d) the term "shock" is used to refer to circulatory shock, septic shock, toxic shock, or any other condition in which oxygen derived radicals lead to inadequate perfusion of vital organs by the circulatory system.
e) the term "oxygen free radical" should be construed as referring to carbon centered radicals, oxygen radicals, or any biomolecule containing an unpaired electron in any discussion of tissue damage.

The compounds of the invention may also be admixed with any inert carrier and utilized in laboratory assays in order to determine the concentration of the compounds within the serum, urine, etc., of the patient as is known in the art. The compounds may also be used as a research tool by forming adducts with molecular oxygen.

EXPERIMENTAL

General Methods

Except where noted otherwise, reagents and starting materials are obtained from common commercial sources and used as received. Tetrahydrofuran (THF) is distilled from sodium-benzophenone ketyl immediately prior to use. Other reaction solvents, and all chromatographic, recrystallization and work-up solvents are spectroscopic grade and used as received. Reactions reported as being run "under $N_2$" are carried out under an atmosphere of dry $N_2$ in oven-dried flasks.

Thin layer chromatography (TLC) is performed on glass-backed, silica gel 60F-254 plates (EM) coated to a thickness of 0.25 mm. The plates are eluted with solvent systems (v/v) as described, and visualized by one or more of the following methods: UV light, $I_2$ vapor, or staining with phosphomolybdic acid, $Ce(SO_4)_2$, $KMnO_4$, or $FeCl_3$ solutions, followed by heating (heat gun). "Thin-Layer Chromatography, a Laboratory Handbook", Egon Stahl, Ed. Springer-Verlag Berlin Heildelberg-New York, 1969. Gas chromatography (GC) is performed on a Hewlett Packard 5890 Series II gas chromatograph equipped with a Hewlett Packard 3392A integrator. Separations are carried out on a 15 m×0.32 mm ID fused silica capillary column (DB-5, 0.25 mm film) from J & W Scientific.

"Concentrated in vacuo" and similar phrases indicate rotary evaporation on a Buchi apparatus at ca. 50° C. and 15–20 Torr (water aspirator), unless stated otherwise. Flash chromatography (FC) is carried out using EM Science silica gel 60(40–63 um) according to the literature procedure. Still, W. C.; Kahn, M.; Mitra, A. *J. Org. Chem.* 1978, 43, 2923.

Melting points are determined on a Thomas Hoover Uni-melt capillary melting point apparatus. Melting points and boiling points are reported uncorrected.

IR spectra are recorded on a Mattson Galaxy Series 5020 infrared spectrophotometer with samples prepared as indicated, and are reported in wavenumbers ($cm^{-1}$). $^1H$ NMR spectra are recorded on a Varian Gemini instrument (300 MHz) with chemical shifts (δ) reported in ppm relative to tetramethylsilane (0.00 ppm) or chloroform (7.26 ppm), unless stated otherwise. Signals are designated as s (singlet), d (doublet), t (triplet), q (quartet), p (pentet), m (multiplet), br (broad), etc. Coupling constants (J) are reported in Hz. First order analyses of spectra are attempted when possible; consequently, chemical shifts and coupling constants for multiplets may only be approximate. $^{13}C$ NMR spectra are recorded on the Varian Gemini instrument (75 MHz) with chemical shifts (δ) reported in ppm relative to chloroform-d (77.00 ppm), unless stated otherwise. Mass spectra (MS) are obtained on a Finnigan MAT Model TSQ 700 Mass Spectrometer System using electron impact or chemical ionization with the molecular ion designated as M given in parentheses.

General Procedure for the Reaction of MeMgBr with Esters (Procedure A).

A solution of MeMgBr (2.5 equiv of a 3 M $Et_2O$ solution) and THF (equal volume) is placed under $N_2$. The solution is cooled to –78° C., and the substrate (1 equiv) is added, either neat or as a solution in THF. The cooling bath is removed, and the reaction mixture is allowed to warm to room temperature (rt). Excess MeMgBr is quenched by adding saturated $NH_4Cl$ solution, and the resulting mixture is poured into dil. HCl and extracted with EtOAc (2×). The organic phase is washed with saturated NaCl solution (brine), dried ($MgSO_4$ or $Na_2SO_4$), filtered and evaporated. The residue is purified as indicated.

General Procedure for the Ritter Reaction (Procedure B).

Powdered NaCN (1.5 to 2.5 equiv) is placed in a dry flask under $N_2$, and cooled in an ice bath. Acetic acid (HOAc) is added, and the mixture is stirred vigorously while a previously prepared mixture of conc. $H_2SO_4$ in an equal volume of HOAc is added through a dropping funnel (Caution! HCN generated). The substrate (1 equiv) is then added, either neat or in a minimum volume of HOAc, the cooling bath is removed, and the mixture is stirred at rt until TLC analysis indicates that the reaction is complete. Excess HCN is then evaporated under a stream of $N_2$ for 1–2 h. The residue is added slowly to a saturated solution of $NaHCO_3$ (vigorous gas evolution), and the mixture is extracted thoroughly with EtOAc. The organic phase is washed with brine, and dried ($Na_2SO_4$), filtered, and concentrated. The residue is purified as indicated.

General Procedure for Cyclization of Formamides (Procedure C).

The formamide (1 equiv) is dissolved in $CH_2Cl_2$ under $N_2$, and cooled in an ice bath. Neat oxalyl chloride (1.1 equiv) is added via syringe, the cooling bath is removed, and the mixture is stirred at rt for 1–2 h. The mixture is then cooled again to 0° C., and solid $FeCl_3$ (1.2 equiv) is added in one portion. The cooling bath is removed, and the mixture is stirred at rt overnight. The resulting reaction mixture is poured into 0.5 M HCl solution and extracted with EtOAc (2×). The organic phase is washed with brine, dried ($Na_2SO_4$), filtered, and evaporated. The residue is taken up in EtOH, treated with a catalytic amount of conc. $H_2SO_4$, and heated at reflux until TLC analysis indicates complete reaction (ca. 3 h). The mixture is then cooled, poured into saturated $NaHCO_3$ solution and extracted with EtOAc (3×). The organic phase is washed with brine, dried ($Na_2SO_4$), filtered, and evaporated. The residue is purified as indicated.

General Procedure for Reduction of Imines (Procedure D).

The imine (1 equiv) is dissolved in MeOH under $N_2$. Solid $NaBH_4$ (1.5 equiv) is added to the solution in small portions (gas and heat evolution). The resulting mixture is stirred at rt for 1–2 h, then added cautiously to 1 M HCl solution. The aqueous phase is washed with EtOAc (discarded), and made basic by adding KOH pellets. The liberated free amine is extracted into EtOAc (3×). The organic phase is washed with brine, dried (Na$_2$SO$_4$), filtered, and evaporated, to give the amine which is used as such.

General Procedure for Oxidation of Amines to Nitrones (Procedure E).

The amine (1 equiv) is dissolved in MeOH and treated sequentially with Na$_2$WO$_4$ (0.1 equiv) and 30% H$_2$O$_2$ (3 equiv). The resulting mixture is stirred at rt until TLC analysis indicates complete reaction (ca. 4 h). The reaction mixture is poured into brine containing Na$_2$S$_2$O$_3$ (to destroy excess peroxide) and extracted several times with EtOAc (until aqueous phase shows little or no product by TLC). The organic phase is dried (Na$_2$SO$_4$), filtered, and evaporated. The crude product is purified as indicated.

General Procedure for Alkylation of Ethyl Isobutyrate (Procedure F).

To a solution of lithium (bis)trimethylsilylamide (LiN (TMS)2, 1 M solution in THF, 1.5 equiv) in THF cooled at −78° C. under N$_2$ is added ethyl isobutyrate (1 equiv). Stirring is continued at −78° C. for 1 h, then 1,3 -dimethyl-3,4,5,6-tetrahydro-2(1H)-pyrimidinone (DMPU, 2% by volume) is added, followed by the electrophile. The cooling bath is removed, and the reaction mixture is stirred overnight. The reaction mixture is poured into cold 1 M HCl and extracted with EtOAc (3×). The organic phase is washed with water and brine, then dried (MgSO$_4$), filtered and evaporated. The residue is purified by FC (CH$_2$Cl$_2$).

General Procedure for Hydrolysis of Ethyl Esters (Procedure G).

The ester (1 equiv) is added to a solution of KOH (2.5 equiv) in 10% aqueous MeOH, and the resulting mixture is heated at reflux until TLC shows the absence of starting material. The mixture is cooled, and most of the MeOH evaporated. The residue is diluted with water and extracted with Et$_2$O (2×, discarded). The aqueous phase is acidified by adding dilute HCl, and extracted with EtOAc (3×). The organic phase is washed with brine, dried (MgSO$_4$), filtered, and evaporated. The crude product is used without further purification.

General Procedure for the Curtius Rearrangement (Procedure H).

To a solution of the carboxylic acid (1 equiv) in toluene at 0° C. and under N$_2$ are added Et$_3$N (0.95 equiv) and diphenyl phosphorylazide (0.95 equiv). The mixture is stirred at 0° C. for 30 min, then heated at reflux for 3 h. The mixture is cooled, washed with cold NaHCO$_3$ solution (2×) and brine (2×), then dried (MgSO$_4$), filtered, and evaporated. The crude product is used without purification.

General Procedure for Reduction of Lactams (Procedure I).

The lactam (1 equiv) is carefully (gas evolution) added to BH$_3$.THF solution (1 M in THF, 2.5 equiv) under N$_2$. After gas evolution subsides, the mixture is heated at reflux overnight. The reaction mixture is cooled, treated cautiously with MeOH (ca. 50% by volume) and 1 M NaOH solution, and heated at reflux for 7 h. The resulting mixture is cooled and extracted with EtOAc (2×). The organic phase is extracted with 1 M HCl (2×), and the aqueous phase is neutralized by adding NaHCO$_3$. The product is extracted into EtOAc (2×), and the organic phase is washed with brine, dried (MgSO$_4$), filtered, and evaporated. The amines are used without further purification.

The following examples further illustrate the reaction sequences described above. However, they should not be construed as limiting the invention in any manner.

EXAMPLE 1

2,2-Dimethyl-1,2-dihydrobenzo[f]isoquinoline N-oxide (9)

2-Methyl-1-naphthalen-1-yl-propan-2-ol (3)

Ester 1 (see Acton, N.; Berliner, E. J. Am. Chem. Soc. 1984, 86, 3312) (20.0 g, 100 mmol) is treated with MeMgBr according to general procedure A. The product 3 is obtained as a white solid, mp 47–48° C., after evaporation of solvent. It requires no further purification. Yield: 19.4 g (97%). $^1$H NMR (CDCl$_3$) 8.16(d,1,J=7.5), 7.85–7.75(m,2), 7.50–7.35(m 4), 3.27(s,2), 1.27(s,6); $^{13}$C NMR (CDCl$_3$) 134.18, 133.96, 133.06, 129.01, 128.60, 127.29, 125.70, 125.42, 125.15, 125.04, 71.64, 45.08, 29.69; MS (MW= 200.3, CI/CH$_4$, eE=70 eV) m/z 200 (M+), 185, 184, 183, 171, 167, 155, 143, 142(base peak), 115, 89.

N-(1,1-Dimethyl-2-naphthalen-1-yl-ethyl)-formamide (5)

Alcohol 3 (3.00 g, 15.0 mmol) is subjected to the Ritter reaction according to general procedure B. The product 5 is obtained as a tan solid, mp 79–80° C., after FC(1:1, exane/EtOAc). Yield: 2.76 g, 81%. The following $^1$H NMR spectrum is for a ca. 70:30 mixture of amide rotamers. Signals for the major rotamer are designated A, and those for the minor rotamer are designated B. $^1$H NMR (CDCl$_3$) 8.18 (d, 0.7, J=8.5, A), 8.05–8.00 (m, 1.3), 7.85–7.75 (m, 2), 7.55–7.33 (m, 4), 5.90 (br d, 0.3, J=9.0, B), 5.25 (br s, 0.7, A), 3.56 (s, 1.4, A), 3.29 (s, 0.6, B), 1.40 (s, 4.2, A), 1.39 (s, 1.8, B); MS (MW=227.3, EI,eE=70 eV) m/z 227 (M+),209, 183, 182, 167, 165, 141, 139, 128, 115, 89, 86(base peak), 76, 63, 58, 42.

2,2-Dimethyl-1,2-dihydrobenzo[f]isoquinoline (7)

Formamide 5 (2.27 g, 10.0 mmol) is cyclized according to general procedure C. The imine 7 (1.61 g, 77%) is obtained as a dark brown solid after flash chromatography (FC) (19:1, CH$_2$Cl$_2$/MeOH). $^1$H NMR (CDCl$_3$) 8.31 (s,1), 8.08 (d, 1, J=7.8), 7.90–7.75 (m, 2), 7.60–7.50 (m, 2), 7.42 (d, 1, J=8.1), 3.12 (s,2), 1.35 (s, 6); $^{13}$C NMR (CDCl$_3$) 157.76, 134.78, 128.57, 126.85, 126.34, 124.32, 124.23, 123.79, 123.41, 54.75, 33.69, 28.49; MS(MW=209.3, EI, e=70eV) m/z 209 (M+, base peak), 194, 181, 167, 152, 139, 115, 97, 82, 75, 63, 41.

2,2-Dimethyl-1,2,3,4-tetrahydrobenzo[f]isoquinoline

Reduction of imine 7(1.61 g, 7.7 mmol) according to general procedure D delivers the amine (1.61 g, 100%) as a dark liquid which is not characterized, but used directly in the next reaction.

2,2-Dimethyl-1,2-dihydrobenzo[f]isoquinoline N-oxide (9)

The crude amine from the previous reaction (1.481 g, 7.024 mmol) is oxidized according to general procedure E to give a tan solid, mp 155–157° C., after recrystallization from 1:9 CH$_2$Cl$_2$/hexane. Yield: 0.866 g(55%). $^1$H NMR (CDCl$_3$) 7.96 (d,1, J=8.3), 7.85–7.75(m,2), 7.81(s,1), 7.55–7.50(m, 2), 7.22(d, 1, J=8.5), 3.45(s,2), 1.54(s,6); $^{13}$C NMR (CDCl$_3$) 133.76, 132.95, 130.75, 128.89, 127.80, 127.09, 126.45, 125.72, 125.47, 123.25, 122.55, 66.89, 38.32, 25.42; MS(EI, eE=70 eV)m/z 225 (M+, base peak), 210, 194, 193, 165, 139, 115, 89, 76, 63, 41; Anal. Calcd for C$_{15}$H$_{15}$NO(MW= 225.3): C,79.97 H,6.71 N,6.22. Found: C,78.79 H,6.66 N,6.22.

EXAMPLE 2

3,3-Dimethyl-3,4-dihydrobenzo[h]isoquinoline N-oxide (10)

2-Methyl-1-naphthalen-2-yl-propan-2-ol (4)

Ester 2 (see Acton, N.; Berliner, E. J. Am. Chem. Soc. 1984, 86, 3312) (7.87 g, 39.3 mmol) is treated with MeMgBr according to general procedure A. The product 4 is obtained as a white solid, mp 79–80° C., after evaporation of solvent. It requires no further purification. Yield: 5.88 g(75%). $^1$H NMR(CDCl$_3$) 7.80–7.75(m,3), 7.66(s,1), 7.45–7.35(m,3), 2.92(s,2), 1.26 (s,6); 13C NMR(CDCl$_3$) 135.37, 133.33, 132.19, 129.06, 128.80, 127.57, 125.96, 125.46, 70.95, 49.80, 29.25; MS(MW=200.3, EI, e=70eV) m/z200 (M+), 185, 167, 165, 143, 142, 141(base peak), 128, 115, 89, 63, 59, 57, 43, 31.

N-(1,1-Dimethyl-2-naphthalen-2-yl-ethyl)-formamide (6)

Alcohol 4 (3.00 g, 15.0 mmol) is treated with NaCN according to general procedure B. The product 6 is obtained as a yellow solid (3.31 g, 97%), mp 59–63° C., after FC (CH$_2$Cl$_2$). The following $^1$H NMR spectrum is for a ca. 67:33 mixture of amide rotamers. Signals for the major rotamer are designated A, and those for the minor rotamer are designated B. $^1$H NMR (CDCl$_3$) 8.10–8.05 (m, 1), 7.80–7.75 (m,3),7.60 (m,1), 7.50–7.45(m,2), 7.30–7.25(m, 1), 5.95(br s, 0.33,B), 5.22(br s, 0.67, A), 3.20 (s,1.3, A), 2.92 (s,0.7, B), 1.40–1.30(m,6); MS (MW=227.3, EI, eE=70 eV) m/z 227(M+), 209, 183, 182, 152, 141, 139, 115, 89, 86 (base peak), 63, 58, 42, 32.

3,3-Dimethyl-3,4-dihydrobenzo[h]lisoquinoline (8)

5 Cyclization of formamide 6 (2.27 g, 10.0 mmol) according to general procedure C furnishes the imine 8 (1.55 g, 74%) as a tan solid which is used without purification. $^1$H NMR (CDCl$_3$) 9.08 (s,1), 8.31 (d 1, J=8.4), 7.90–7.85 (m,2), 7.60–7.55 (m,1), 7.50 (m,1), 7.29 (s,1), 2.88 (s,2), 1.30 (s,6); 13C NMR(CDCl$_3$) 153.38, 134.69, 132.61, 131.07, 129.12, 128.50, 127.04, 126.44, 125.18, 121.34, 121.02, 53.97, 38.59, 27.71; MS(MW=209.3, EI, eE=70 eV) m/z 209(M+, base peak), 194, 180, 167, 152, 139, 115, 97, 82, 76, 63, 51, 41.

3,3-Dimethyl-1,2,3,4-tetrahydrobenzo[h]isoquinoline

Reduction of imine 8(1.47 g, 7.03 mmol) according to general procedure D delivers the amine (1.47 g, 99%) as a dark liquid which is not characterized, but used directly in the next reaction.

3,3-Dimethyl-3,4-dihydrobenzo[h]isoquinoline N-oxide (10)

The crude amine from the previous reaction (1.47 g, 6.97 mmol) is oxidized according to general procedure E to afford a yellow solid, mp 157–159° C., after recrystallization from 1:9 CH$_2$Cl$_2$/hexane. Yield: 0.950 g (61%). $^1$H NMR (CDCl$_3$) 8.51(s,1), 7.97(d,1,J=8.5), 7.85–7.75(m,2), 7.55–7.50(m,2), 7.31(d,1,J=8.3), 3.21(s,2), 1.50(s,6); $^{13}$C NMR(CDCl$_3$) 132.64, 129.51, 129.27, 128.75, 128.15, 127.58, 125.90, 125.63, 123.06, 121.28, 66.15, 42.34, 24.45; MS(CI/CH$_4$, eE=70eV) m/z 226[(M+H)+,base peak], 210, 193, 167, 152; Anal. Calcd for C$_{15}$H$_{15}$NO(MW=225.3): C,79.97 H,6.71 N,6.22. Found: C,79.58 H,6.72 N,6.02.

EXAMPLE 3

3,4-Dihydroisoquinoline-3-spiro-4'-tetrahydropyran N-oxide (11)

4-Benzyltetrahydropyran-4-ol (17)

Tetrahydropyran-4-one (4.34 g, 43.4 mmol) is treated with benzylmagnesium chloride (2 M in THF, 32.5 mL, 65.0 mmol) according to general procedure A. The crude product is filtered through silica gel, first with CH$_2$Cl$_2$, then with 1:1 hexane/EtOAc, to give alcohol 17 as a colorless oil (7.3 g, 87%). $^1$H NMR (CDCl$_3$) 7.40–7.15(m,5), 3.80–3.65(m,4), 2.77(s,2), 1.81(s,1), 1.80–1.70(m,2), 1.50–1.40(m,2); $^3$C NMR(CDCl$_3$) 135.90, 130.53, 128.32, 126.74, 68.55, 63.65, 49.42, 37.46; MS(MW=192.3, CI/CH$_4$, eE=70eV) m/z 193 (M+H)+, 191, 176, 175(base peak), 157, 145, 129, 119, 101, 92, 83, 71.

N-(4-Benzyltetrahydropyran-4-yl)-formamide (19)

Tertiary alcohol 17 (13.9 g, 72.4 mmol) is treated with NaCN according to general procedure B. TLC analysis (1:1 hexane/EtOAc) indicates that 17 is completely converted into a high R$_f$ product within a few hours. Prolonged stirring of the reaction mixture first at rt(5 days), then at 50° C. (16 h), gives only a small amount of a lower R$_f$ product. The reaction is worked up by the general method, and the mixture is purified by filtration through silica gel with 1:1 hexane/EtOAc. The material (8.0 g, 64%) proves to be ($^1$H NMR) a ca. 1:1 mixture of olefin isomers formed by simple elimination of water from 17. Further elution of the silica gel with 10:1 CH$_2$Cl$_2$/MeOH yields a small amount of the formamide (19, 1.8 g, 11%). The mixture of olefins is resubmitted to the general Ritter reaction conditions (but at rt for 5 days, then at 45–50° C. for 16 h) to give 5.5 g of 19 as a yellow oil after FC (10:1 CH$_2$Cl$_2$/MeOH). The total yield of 19 from 17 is therefore 7.3 g(46%). The following NMR spectra are for a a. 75:25 mixture of amide rotamers. Signals for the major rotamer are designated A, and those for the minor rotamer re designated B. $^1$H NMR (CDCl$_3$) 8.13(s,0.75,A), 7.80(d,0.25, J=12.3,B), 7.45–7.00(m,5 total), 6.02(br d,0.25,J=12.3,B), 5.25 (br s,0.75,A), 3.90–3.50(m,4 total), 3.08 (s,0.75, A), 2.85(s,0.25, B), 2.15–1.65 (m, 4 total); $^{13}$C NMR (CDCl$_3$) 163.76 (B), 161.29 (A), 136.13 (A), 134.52 (B), 131.30 (B), 130.82 (A), 130.70 (B), 130.56 (B), 128.36 (A), 128.14 (B), 127.99 (A), 127.84 (B), 127.11 (B), 126.54 (A), 63.19 (A), 62.76 (B), 54.38 (A), 52.93 (B), 49.60 (B), 43.87 (A), 36.11 (B), 34.98 (A); MS(MW=219.3, EI,eE=70 eV) m/z 220 (M+H)$^+$, 201, 174, 141, 128(base peak), 115, 100, 98, 91, 82, 70, 65, 53, 42.

3,4-Dihydroisoquinoline-3-spiro-4'-tetrahydropyran (21)

Formamide 19 (1.00 g, 4.57 mmol) from the previous experiment is cyclized according to general procedure C to give the imine 21 as a yellow oil after FC (1:1 hexane/EtOAc, then EtOAc). The yield is 0.38 g (41%). $^1$H NMR (CDCl$_3$) 8.35(s,1), 7.45–7.30(m,3), 7.16(d,1,J=7.0), 4.05–3.95(m,2), 3.80–3.70(m,2), 2.75(s,2), 1.80–1.60(m,4); 13C NMR (CDCl$_3$) 158.21, 134.50, 131.33, 128.25, 128.05, 127.18, 127.13, 63.72, 53.85, 37.29, 37.13; MS(MW=201.3, EI, eE=70 eV) m/z 201(M+), 200, 186, 170, 156 (base peak), 144, 118, 115, 102, 89, 77, 63, 51, 41.

1,2,3,4-Tetrahydroisoguinoline-3-spiro-4'-tetrahydropyran

Imine 21 (1.90 g, 9.45 mmol) from the previous reaction is reduced according to general procedure D. The amine is extracted into 1 M HCl and washed with EtOAc (discarded). The aqueous phase is then made basic (pH 8) by adding KOH pellets, saturated with NaCl, and extracted with EtOAc (3×). The organic phase is washed with brine, dried (Na$_2$SO$_4$), filtered and evaporated. The resulting white solid (1.76 g, 92%) requires no further purification. $^1$H NMR (CDCl$_3$) 7.20–7.00(m,4), 4.01(s,2), 3.95–3.80(m,2), 3.75–3.65(m,2), 2.70(s,2), 1.75–1.50(m,5); $^{13}$C NMR (CDCl$_3$) 134.78, 133.42, 129.74, 126.16, 125.93, 125.71, 63.70, 48.23, 43.23, 40.17, 36.13; MS(MW=203.3, EI, eE=70 eV) m/z 203(M+, base peak), 174, 158, 145, 144, 128, 104, 103, 91, 78, 72, 65.

3,4-Dihydroisoquinoline-3-spiro-4'-tetrahydropyran N-oxide (11)

The amine (0.292 g, 1.438 mmol) from the previous reaction is oxidized according to general procedure E. The crude product is purified by FC (20:1 CH$_2$Cl$_2$/MeOH and recrystallization from hexane/CH$_2$Cl$_2$ to furnish the nitrone, MDL 105,992 (0.205 g, 66%), as white crystals, mp 135–136° C. $^1$H NMR (CDCl$_3$) 7.76(s,1), 7.35–7.10(m,4), 4.04(dt,2,J=11.8, 4.5), 3.65(ddd,2,J=12.0, 11.7, 3.0), 3.24(s, 2), 2.49(ddd,2, J=13.7, 10.2, 4.5), 1.60(br d, 2, J=13.7); $^{13}$C NMR (CDCl$_3$) 132.92, 129.22, 128.89, 128.03, 127.73, 127.69, 124.68, 66.83, 64.11, 37.16, 32.15; MS(EI,eE=70eV) m/z 217(M+),200, 172, 170, 156 (base peak), 144, 128, 115, 102, 89, 77, 63, 51, 41; Anal. Calcd for C$_{13}$H$_{15}$NO$_2$ (MW=217.3): C,71.87 H,6.96 N,6.45. Found: C,71.79 H,6.96 N,6.54.

EXAMPLE 4

4,5-dihydro-3H-benzo[c]azepin-3-spiro-4'-tetrahydropyran N-oxide (12)

4-Phenethyltetrahydropyran-4-ol (18)

Magnesium turnings (2.34 g, 97.6 mmol) and THF(100 mL) are placed under N$_2$. A small crystal of I$_2$ and a 1 mL portion of phenethyl bromide are added, and the mixture is stirred at rt for 30 min. The reaction mixture is briefly heated with a heat gun until the iodine color is discharged. An exothermic reaction commences. Thereafter, the remaining bromide (10.5 mL, total=11.5 mL, 84.6 mmol) is added at a rate to maintain a gentle reflux (ca. 10 min). When the mixture reaches rt, the reaction apparatus is placed in an ice water bath, and tetrahydropyran-4-one (6.0 mL, 43.4 mmol) is added to the reaction mixture neat via syringe over a five minute period. The cooling bath is removed, and the reaction mixture is allowed to reach rt. The reaction mixture is worked up and purified as above with compound 17 to give the product 18. Recrystallization from hexane/CH$_2$Cl$_2$ gives 18 as white needles (1 crop), mp 74–75° C. (5.0 g, 37%). $^1$H NMR (CDCl$_3$) 7.40–7.10(m,5), 3.90–3.70(m,4), 2.80–2.65 (m,2), 1.90–1.70(m,4), 1.55(br d,2, J=11.9), 1.46(s,1); $^{13}$C NMR (CDCl$_3$) 142.14, 128.47, 128.28, 125.87, 68.86, 63.78, 45.13, 37.58, 28.91; MS(CI/CH$_4$, eE=70eV) m/z 207(M+H)+,205, 190, 189 (base peak), 171, 161, 143, 119, 101, 91, 83, 71; Anal. Calcd for C$_{13}$H$_{18}$O$_2$ (MW=206.3): C,75.69 H,8.80. Found: C,75.46 H,8.80.

N-(4-Phenethyltetrahydropyran-4-yl)-formamide (20)

Tertiary alcohol 18 (3.11 g, 15.1 mmol) is treated with NaCN according to general procedure B. The reaction time is 5 days. The product is purified by FC (eluting first with CH$_2$Cl$_2$, then with EtOAc, and finally with 10:1 CH$_2$Cl$_2$/MeOH) to provide a yellow oil,(20, 2.70 g, 77%) The following NMR spectrum is for a ca. 67:33 mixture of amide rotamers. Signals for the major rotamer are designated A, and those for the minor rotamer are designated B. H NMR (CDCl$_3$) 8.29(d,0.33, J=10,B), 8.19(s,0.67,A), 7.40–7.10(m, 5), 6.77(d,0.33, J=10,B), 5.71(s,0.67 A), 3.95–3.55(m,4), 2.80–2.55(m,2), 2.30–1.65(m,6); MS(MW=233.3,CI/CH$_4$, eE=120eV) m/z 234 [(M+H)$^+$, base peak], 233, 217, 199, 189, 171, 161, 145, 129, 119, 100, 91, 74.

4,5-dihydro-3H-benzo[c]azepin-3-spiro-4'-tetrahydropyran (22)

Formamide 20 (3.65 g, 15.7 mmol) from the previous experiment is cyclized according to general procedure C to give imine 22 (0.47 g, 14%) as a yellow oil after FC (10:1 CH$_2$Cl$_2$/iPrOH). $^1$H NMR (CDCl$_3$) 8.35(s,1), 7.50–7.45(m, 1) 7.40–7.20(m,3), 4.10–3.95(m,2), 3.85–3.70(m,2), 3.15–3.05(m,2), 2.00–1.95(m,2), 1.85–1.70(m,4); $^{13}$C NMR (CDCl$_3$) 157.88, 141.77, 135.23, 132.61, 129.89, 129.66, 126.21, 64.02, 58.32, 38.71, 37.25, 30.13; MS(MW=215.3, CI/CH$_4$, eE=120 eV) m/z 216 [(M+H+), base peak], 199, 189, 171, 143, 117, 100, 83.

1,2,4,5-tetrahydro-3H-benzo[c]azepin-3-spiro-4'-tetrahydropyran

Imine 22 (0.430 g, 2.00 mmol) from the previous reaction is reduced according to general procedure D. The product is isolated after an acid/base work-up as described above for the reduction of 21. The resulting white crystals, mp 76–78° C., weigh 0.427 g (98%). $^1$H NMR(CDCl$_3$) 7.20–7.05(m,4), 3.89(s,2), 3.88–3.75(m,2), 3.70–3.60(m,2), 2.90–2.80(m,2), 1.80–1.55(m,6), 1.23(br s,1); $^{13}$C NMR(CDCl$_3$) 142.69, 141.94, 129.21, 127.88, 126.85, 126.00, 63.35, 52.14, 46.70, 40.44, 36.92, 29.34; MS (MW=217.3, CI/CH$_4$, eE=120eV) m/z 218[(M+H)+, base peak], 216, 201, 183, 157, 118, 91.

4,5-dihydro-3H-benzo[c]azepin-3-spiro-4'-tetrahydropyran N-oxide (12)

The amine (0.420 g, 1.94 mmol) from the previous reaction is oxidized according to general procedure E to furnish the nitrone, MDL 104,129 (0.225 g, 51%), as a tan solid, mp 107–109° C. $^1$H NMR(CDCl$_3$) 7.95(s,1), 7.40–7.05(m,4), 4.10–3.90(m,2), 3.70–3.60(m,2), 3.15–3.00 (m,2), 2.70–2.55(m,2), 2.45–2.35(m,2), 1.80–1.60(m,2); $^{13}$C NMR(CDCl$_3$) 139.36, 138.60, 130.98, 129.60, 128.90, 126.76, 72.05, 64.24, 34.73, 34.59, 29.29; MS (CI/CH$_4$, eE=120eV) m/z 232 [(M+H)+, base peak], 214, 199, 181, 158, 116, 98, 83; Anal. Calcd for C$_{14}$H$_{17}$NO$_2$ (MW=231.3): C,72.70 H,7.41 N,6.06. Found: C,72.36 H,7.38 N,6.00.

EXAMPLE 5

5,5-Dimethyl-4,5-dihydrothieno[2,3-c]pyridine N-oxide (13)

2-Methyl-1-thiophen-3-yl-propan-2-ol (25)

The ethyl ester of thiophene-3-acetic acid (15.0 g, 88.2 mmol) is treated with MeMgBr according to general procedure A. The product 25 is obtained as a colorless liquid (16.1 g, 88%) which requires no further purification. $^1$H NMR (CDCl$_3$) 7.25–7.20(m,1), 7.00–6.95 (m,2), 2.77(s,2), 1.21(s, 6); $^{13}$C NMR(CDCl$_3$) 138.39, 130.18, 125.39, 123.12, 70.77, 44.42, 29.37; MS(MW=156.2, EI, eE=70eV) m/z 156 (M+), 141, 139, 100, 98 (base peak), 97, 85, 69, 59, 43, 32.

5,5-Dimethyl-4,5-dihydrothieno[2,3-c]pyridine (26)

Treatment of the alcohol 25 from the previous reaction (15.9 g, 102 mmol) with NaCN according to general procedure B gives the cyclized imine directly as a dark liquid after FC (3:1 hexane/EtOAc). Yield: 4.15 g (25%). $^1$H NMR (CDCl$_3$) 8.17(s,1), 7.36(d,1, J=4.8), 6.88(d,1,J=4.8), 2.75(s, 2), 1.28(s,6); $^{13}$C NMR (CDCl$_3$) 153.96, 141.02, 131.45, 125.79, 124.39, 56.24, 35.65, 28.03; MS(MW=165.3, EI, eE=70eV) m/z 165 (M+, base peak), 150, 138, 124, 123, 97, 86, 77, 69, 58, 45.

5,5-Dimethyl-4,5,6,7-tetrahydrothieno[2,3-c]pyridine

Reduction of the imine 26 from the previous reaction (1.00 g, 6.1 mmol) according to general procedure D provides the corresponding amine (1.00g, 100%) as a dark liquid (MW=167.3) which is used without further purification. $^1$H NMR(CDCl$_3$) 7.13(d,1, J=5.1), 6.75 (d,1, J=5.1), 4.07(s,2), 2.56(s,2), 2.37(s,1), 1.23(s,6).

5,5-Dimethyl-4,5-dihydrothieno[2,3-c]pyridine N-oxide (13)

The crude amine from the previous reaction (1.00 g, 5.99 mmol) is oxidized according to general procedure E to afford a tan solid (300 mg, 28%, mp 136–138° C.) after FC (19:1 CH$_2$Cl$_2$/MeOH). $^{13}$H NMR (CDCl$_3$) 7.73(s,1), 7.33(d,1, J=4.9), 6.93 d,1, J=4.9), 3.04(s,2), 1.48(s,6); $^{13}$C NMR (CDCl$_3$) 132.25, 128.30, 127.52, 127.14, 126.64, 68.03, 38.24, 25.25; MS(EI,eE=70eV) m/z 181 (M+, base peak), 166, 149, 138, 134, 110, 96, 91, 77, 65, 51, 45; Anal. Calcd for C$_9$H$_{11}$NOS (MW=181.3): C,59.64 H,6.12 N,7.73 S,17.69. Found: C,59.57 H,6.10 N,7.86 S,17.56.

EXAMPLE 6

4,5-dihydro-3H-benzo[c]azepine-3-spirocyclohexane N-oxide (14)

1-Phenethylcyclohexan-1-ol

Reaction of cyclohexanone (13.2 g, 135 mmol) with phenethylmagnesium bromide as described above for compound 18 affords the tertiary alcohol (16.0 g, 58%) after FC (19:1 cyclohexane/EtOAc, then 9:1 cyclohexane/EtOAc). MS(CI/CH$_4$, eE=70 eV) m/z 203 (M–H)$^+$, 187 (M+H–H$_2$O, base peak).

N-(1-Phenethylcyclohex-1-yl)-formamide

The alcohol from the previous reaction (15.9 g, 77.8 mmol) is submitted to the Ritter reaction according to general procedure B. The formamide is obtained as an orange paste (12.4 g, 69%) after FC (4:1 cyclohexane/EtOAc, then EtOAc). The following $^1$H NMR spectrum is for a mixture of amide rotamers. $^1$H NMR (CDCl$_3$) 8.27 and 8.17 (2 d, 1 total, J=12.5 and 2.1), 7.30–7.15 (m,5), 5.81 and 5.10 (br d and br s,1 total, J=12.5), 2.65–2.55 (m,2), 2.15–2.10 (m,2), 1.90–1.85 (m,1), 1.80–1.75 (m,1), 1.65–1.30 (m,8); IR (thin film) 3295, 2932, 2859, 1667, 1537, 1497, 1454, 1391, 700; MS (MW=231.3, EI, eE=70 eV) m/z 231 (M$^+$), 188, 126, 104 (base peak), 91, 81.

4,5-dihydro-3H-benzo[c]azepine-3-spirocyclohexane

The formamide (13.0 g, 56.2 mmol) from the previous experiment is cyclized according to general procedure C, except that the oxalate moiety is cleaved by heating the neat intermediate at 125° C. until gas evolution subsides (ca. 2 h). The imine (8.95 g, 75%) is obtained as an orange liquid. $^1$H NMR (CDCl$_3$) 8.28 (s,1), 7.50–7.40 (m,1), 7.30–7.20 (m,3), 3.05–3.00 (m,2), 1.95–1.90 (m,2), 1.80–1.70 (m,4), 1.55–1.40 (m,6); $^{13}$C NMR (CDCl$_3$) 157.06, 142.12, 135.05, 132.78, 129.60, 129.57, 126.01, 61.03, 38.07, 34.69, 30.57, 26.06, 22.15; MS (MW=213.3, CI/CH$_4$, eE=70 eV) m/z 214 [(M$^+$H)$^+$, base peak], 197, 141, 129.

1,2,4,5-tetrahydro-3H-benzo[c]azepine-3-spirocyclohexane

Reduction of the imine from the previous reaction (8.9 g, 4 mmol) according to general procedure D furnishes the amine (7.6 g, 84%) as a pale yellow liquid which is not purified. $^1$H NMR (CDCl$_3$) 7.15–7.05 (m,4), 3.89 (s,2), 2.90–2.85 (m,2), 1.70–1.35 (m,12); 13C NMR (CDCl$_3$) 142.66, 142.22, 129.17, 127.89, 126.58, 125.78, 54.02, 46.73, 39.22, 36.48, 29.75, 26.44, 21.60; MS (MW=215.3, CI/CH$_4$, eE=70 eV) m/z 216 [(M$^+$H)$^+$, base peak], 117.

4,5-dihydro-3H-benzo[c]3azepine-3-spirocyclohexane N-oxide (14)

The amine from the previous reaction (1.36 g, 6.32 mmol) is oxidized according to general procedure E to give the nitrone (1.0 g, 69%) as cream crystals, mp 123–126° C., after FC (EtOAc). $^1$H NMR (CDCl$_3$) 7.94 (S,1), 7.25–7.10 (m,4), 3.05–3.00 (m,2), 2.55–2.45 (m,2), 2.30–2.25 (m,2), 1.80–1.60 (m,5), 1.50–1.35 (m,3); 13C NMR (CDCl$_3$) 140.29, 139.42, 131.53, 129.37, 128.63, 128.18, 126.57, 75.68, 34.13, 31.55, 29.21, 24.89, 22.36; MS (EI, eE=70 eV) m/z 229 (M$^+$), 212 (base peak), 170, 141, 130, 117, 104, 77; Anal. Calcd for C$_{15}$H$_{19}$NO (MW=229.3): C,78.57 H,8.35 N,6.11. Found: C,78.64 H,8.32 N,6.47.

EXAMPLE 7

3,3,5,7-Tetramethyl-3,4-dihydroisoquinolin-6-ol N-oxide (15)

Methyl (3-hydroxyphenyl) acetate (28)

Phenol-3-acetic acid (13.3 g, 87.3 mmol) is dissolved in MeOH (75 mL), and 10 drops of conc. H$_2$SO$_4$ are added. The mixture is stirred at rt overnight, then added cautiously to dilute NaHCO$_3$ solution and extracted with EtOAc (2×). The organic extract is washed with brine, and dried (MgSO$_4$), filtered, and evaporated to give 28 as a light yellow oil (14.5 g, 100%, MW=166.2), which is pure enough to carry on. $^1$H NMR (CDCl$_3$) 7.17 (t, 1, J=7.7), 6.85–6.70(m,3), 3.70 (s,3), 3.58 (s,2); $^{13}$C NMR (CDCl$_3$) 172.55, 155.92, 135.24, 129.77, 121.45, 116.20, 114.30, 52.26, 41.03.

3-(2-Hydroxy-2-methylpropyl)phenol (29)

The ester 28 from the previous reaction (14.5 g, 87.3 mmol) is treated with MeMgBr (3 M in Et$_2$O, 150 mL, 450 mmol) according to general procedure A. Vigorous mechanical stirring is required to prevent solidification of the reaction mixture. The substrate (in THF) is added (vigorous gas evolution) via syringe over 15 min. The resulting crude product is dissolved in warm CH$_2$Cl$_2$ and diluted with hexane to produce 29 as a white, crystalline solid, mp 91–94° C. (12.3 g, 85%). $^1$H NMR (CDCl$_3$) 7.14 (t, 1, J=7.7), 6.80–6.68 (m,3), 2.70 (s,2), 1.23 (s,6); $^{13}$C NMR (CDCl$_3$) 155.92, 138.97, 129.41, 122.61, 117.31, 113.78, 71.54, 49.36, 28.98; MS (EI, eE=70 eV) m/z 166 (M$^+$), 152, 151, 133, 115, 108 (base peak), 107, 90, 79, 77, 63, 59, 51, 43; Anal. Calcd for C$_{10}$H$_{14}$O$_2$ (MW=166.2): C,72.26 H,8.49. Found: C,72.04 H,8.38.

4-Bromo-3-(2-hydroxy-2-methylpropyl)phenol (30)

Alcohol 29 (12.3 g, 74.2 mmol) is dissolved in dry DMF and cooled to 0° C. under N$_2$. Solid N-bromosuccinimide (NBS, 14.77 g, 83.0 mmol) is added in small portions (the yellow color is allowed to dissipate between additions) over 1.5 h. After the addition is complete, stirring at 0° C. is continued for 30 min. The mixture is then poured into water and extracted with EtOAc (3×). The organic phase is washed with water (1×) and brine (1×), dried (MgSO$_4$), filtered, and evaporated. The residue is dissolved in EtOAc/CH$_2$Cl$_2$ and diluted with hexane to afford 30 as white crystals, mp 139–141° C. (12.7 g, 70%). Concentration of the mother liquor gives two more crops (1.2 and 1.0 g) of crystals, bringing the total to 14.9 g (82%). $^1$H NMR (acetone-d6, 2.05 ppm) 8.43 (S,1), 7.34 (d, 1, J=8.7), 7.01 (d, 1, J=2.7), 6.64 (dd, 1, J=8.7, 2.8), 2.89 (s,2), 1.21 (s,6); $^{13}$C NMR (acetone-d6, 20.83 ppm) 147.90, 130.98, 124.56, 111.34, 107.05, 106.19, 62.35, 39.59, 20.76; MS (EI, eE=70 eV) m/z 246/244 (M$^+$), 231/229, 201, 188/186, 163, 150, 131, 108, 107, 91, 77, 63, 59 (base peak), 51, 43; Anal. Calcd for C$_{10}$H$_{13}$BrO$_2$ (MW=245.1): C,49.00 H,5.35. Found: C,49.03 H,5.20.

4-Bromo-3-(2-hydroxy-2--methylpropyl)-2,6-(bispyrrolidin-1 ylmethyl)phenol (32)

The bromophenol 30 from the previous step (5.7 g, 23.3 mmol) and pyrrolidine (4.8 mL, 58.2 mmol) are placed in a flask with a reflux condenser and under N$_2$. Aqueous formaldehyde (4.7 mL, 58.2 mmol) is added to the mixture, causing a vigorous exothermic reaction. The yellow mixture is stirred and heated at ca. 85° C. for 6 h, with additional 2 equivalent portions of pyrrolidine and formaldehyde being added after 3 h. The reaction mixture is cooled, poured into water, and extracted with EtOAc (3×). The organic phase is washed with brine and dried (Na$_2$SO$_4$), filtered, and evaporated. The residue is taken up in CH$_2$Cl$_2$ and diluted with hexane to afford 32 as white crystals, mp 111–113° C. Two more crops of crystals are obtained upon concentration of the mother liquor. The total yield of 32 is therefore 8.0 g (83%). $^1$H NMR (CDCl$_3$) 8.50 (br s,1), 7.19 (s,1), 3.75 (v br s,8), 3.16 (v br s,2), 2.62 (v br s,8), 1.84 (br s,4), 1.78 (br s,4), 1.38 (v br s,6); $^{13}$C NMR (CDCl$_3$) 156.28, 139.24, 131.02, 125.82, 121.77, 115.82, 68.68, 58.08, 53.30, 52.33, 49.13, 46.78, 34–28 (v br, gem dimethyl), 23.69, 23.23; MS (CI/CH$_4$, eE=70 eV) m/z 413/411 (M$^+$H)$^+$, 397/395, 395/

393, 370/368, 342/340 (base peak), 324/322, 290, 283, 262, 211, 183, 145, 100; Anal. Calcd for $C_{20}H_{31}BrN_2O_2$ (MW= 411.4): C,58.39 H,7.60 N,6.81. Found: C,58.44 H,7.70 N,6.75.

3-(2-Hydroxy-2-methylpropyl)-2,6-bis[(4-methoxybenzylsulfanyl)methyl]phenol (37)

The bis(pyrrolidine) compound 32 (5.00 g, 12.17 mmol) and 4-methoxybenzyl mercaptan (11.24 g, 73.0 mmol) are combined in a flask equipped with a reflux condenser, and under $N_2$. The mixture is stirred and heated at 180° C. (sand bath in heating mantle) for 3 h, then cooled, diluted with $CH_2Cl_2$, and applied to a pad of silica gel. The nonpolar impurities are eluted with $CH_2Cl_2$, then the crude product is eluted with 10:1 $CH_2Cl_2$/iPrOH. The material can be further purified by FC (4:1, $CH_2Cl_2/CH_3CN$) to give 37 as a pale yellow oil (4.60 g, 76%). $^1$H NMR (CDCl$_3$) 7.26 (d, 2, J=8.5), 7.18 (d, 2, J=8.6), 7.00–6.80 (m, 6), 6.71 (d, 1, J=7.8), 3.85 (s, 2), 3.80 (s, 3), 3.79 (s, 3), 3.72 (s, 2), 3.66 (s, 2), 3.59 (s, 2), 2.68 (s, 2), 1.53 (s, 1), 1.15 (s, 6); $^{13}$C NMR (CDCl$_3$) 158.69, 154.13, 137.28, 130.00, 129.51, 128.90, 124.54, 123.80, 121.70, 114.21, 113.92, 113.88, 71.02, 55.24, 55.21, 45.31, 36.21, 34.93, 31.78, 29.54, 27.69; MS (MW=498.7, CI/CH$_4$, eE=70 eV) m/z 499 (M$^+$H)$^+$, 481, 427, 389, 346, 327, 287, 237, 207, 175, 155, 122, 121 (base peak), 109, 91.

3-(2-Hydroxy-2-methylpropyl)-2,6-dimethylphenol (33)

Raney nickel (RaNi, ca. 20 g) is washed five times with water and twice with anhydrous EtOH. A slurry of this catalyst in EtOH is then added to a solution of bis(sulfide) 37 (3.01 g, 6.04 mmol) in EtOH (30 mL). The resulting mixture is heated at vigorous reflux under $N_2$ for 2 h, then cooled. The supernatant is decanted, and the catalyst is washed successively with MeOH and EtOAc (2×). The decanted organic layers are combined and evaporated. The residue is purified by FC (10:1, $CH_2Cl_2$/iPrOH) to give 33 as a pale yellow oil (0.98 g, 84%). $^1$H NMR (CDCl$_3$) 6.94 (d, 1, J=7.7), 6.72 (d, 1, J=7.7), 2.81 (s, 2), 2.24 (s, 6), 1.24 (s, 6); $^{13}$C NMR (CDCl$_3$) 152.44, 135.06, 127.42, 123.42, 122.91, 120.95, 71.59, 45.68, 29.41, 15.87, 12.76; MS (MW=194.3, CI/CH$_4$, eE=70 eV) m/z 195 (M$^+$H)$^+$, 177 (base peak), 175, 149, 136, 91, 79.

3,3,5,7-Tetramethyl-3,4-dihydroisoquinolin-6-ol (38)

Tertiary alcohol 33 (12.5 g, 64.4 mmol) is subjected to the Ritter reaction according to general procedure B. The substrate is added to the acid/cyanide mixture (at rt) over a 2.5 h period, and the resulting red reaction mixture is stirred overnight at rt. Because of the high water solubility of the product, during the work-up the aqueous phase is saturated with NaCl, and extracted six times with EtOAc to obtain an acceptable recovery of material. The organic phase is dried (Na$_2$SO$_4$), filtered and concentrated. The residue is filtered through silica gel with 10:1 $CH_2Cl_2$/MeOH, and the appropriate fractions are combined and diluted with hexane to produce 38 as yellow crystals, mp 220–234° C. (dec.). A lower R$_f$ product is also isolated. This product displays the same type of TLC behavior (blue fluorescence), and a very similar $^1$H NMR spectrum, and is thought to be a symmetrical dimer. Upon standing in solution, this product is slowly converted into 38, which then precipitates. Three crops of the yellow crystals are collected for a total yield of 6.8 g (52%). $^1$H NMR (CD$_3$OD, 3.30 ppm) 7.76 (s, 1), 7.10 (s, 1), 4.93 (s, 1), 2.82 (s, 2), 2.10 (s, 3), 2.07 (s, 3), 1.33 (s, 6); $^{13}$C NMR (CD$_3$OD, 49.05 ppm) 158.21, 136.17, 134.91, 127.55, 126.90, 54.34, 38.15, 27.25, 17.02, 11.39; MS (MW=203.3, CI/CH$_4$, eE=70 eV) m/z 204 [(M$^+$H)$^+$, base peak)], 188, 177, 122.

3,3,5,7-Tetramethyl-1,2,3,4-tetrahydroisoquinolin-6-ol

Imine 38 (1.00 g, 4.93 mmol) is hydrogenated (50 psi H$_2$) over RaNi (spatula scoop, washed 3×with water and 3×with EtOH) in EtOH (20 mL) for 2 h at rt. Filtration of the reaction mixture through filter aid and evaporation of the solvent gives the amine as a light yellow solid (MW=205.3) which is used without further purification. Yield: 0.90 g (89%). $^1$H NMR (CDCl$_3$) 6.68 (s, 1), 3.95 (s, 2), 3.62 (br s, 2), 2.45 (s, 2), 2.21 (s, 3), 2.08 (s, 3), 1.20 (s, 6); $^{13}$C NMR (CDCl$_3$) 150.43, 131.39, 125.87, 125.12, 122.19, 121.16, 48.85, 43.93, 38.98, 27.89, 16.01, 10.97.

3,3,5,7-Tetramethyl-3,4-dihydroisoquinolin-6-ol N-oxide (15)

The amine from the previous reaction (0.90 g, 4.39 mmol) is oxidized according to general procedure E. The nitrone is obtained (0.66 g, 69%) as light yellow crystals, mp 225–240° C. $^1$H NMR (CDCl$_3$) 7.60 (s, 1), 6.80 (s, 1), 2.97 (s, 2), 2.23 (s, 3), 2.17 (s, 3), 1.44 (s, 6); 13C NMR (DMSO-d$_6$, 39.43 ppm) 154.11, 130.78, 127.31, 124.66, 122.66, 122.44, 120.40, 64.87, 38.14, 24.35, 16.50, 11.60; MS (EI, eE=70 eV) m/z 219 (M$^+$, base peak), 202, 187, 172, 160, 115, 91, 77, 43; Anal. Calcd for $C_{13}H_{17}NO_2$ (MW= 219.3) C, 71.21 H, 7.81 N, 6.39. Found: C, 71.25 H, 7.70 N, 6.35.

EXAMPLE 8

3,3,6,8-Tetramethyl-4,5-dihydro-3H-benzo[c]azepin-7-ol, N-oxide (16)

Methyl-3'-hydroxycinnamate (41)

To a solution of 3'-hydroxycinnamic acid 40 (24.5 g, 149 mmol) in MeOH (200 mL) is added conc. H$_2$SO$_4$ (2 mL). The resulting solution is stirred overnight at rt, then poured into saturated, aqueous NaHCO$_3$ solution and extracted with EtOAc (2×). The organic phase is dried (MgSO$_4$), filtered and concentrated to give a brown powder (22.8 g, 86%). A sample can be cystallized from cyclohexane/EtOAc to provide 41 as a cream crystalline powder, mp 84–87° C. $^1$H NMR (CDCl$_3$) 7.65 (d, 1, J=16.0), 7.30–7.25 (m, 1), 7.10–7.05 (m, 1), 7.03 (m, 1), 6.90 (ddd, 1, J=8.1, 2.5, 0.9), 6.41 (d, 1, J=16.0), 5.90 (s, 1), 3.82 (s, 3); $^{13}$C NMR (CDCl$_3$) 167.90, 156.20, 145.01, 135.77, 130.12, 120.73, 117.90, 117.64, 114.58, 51.92; MS (CI/CH$_4$, eE=70 eV) m/z 179 [(M$^+$H)$^+$, base peak)], 147; Anal. Calcd for $C_{10}H_{10}O_3$ (MW=178.2): C, 67.14 H, 5.66. Found: C, 67.40 H, 5.68.

3-(3-hydroxyphenyl)propionic acid methyl ester (42)

Ester 41 (22.8 g, 128 mmol) is dissolved in MeOH (250 mL) and placed in a Parr bottle with 5% Pd/C (2.0 g). The mixture is hydrogenated on a Parr apparatus for 90 min at 50 psi H$_2$ and rt. The reaction mixture is filtered and evaporated to give 42 as a dark gray liquid (19.5 g, 84%). $^1$H NMR (CDCl$_3$) 7.15 (t, 1, J=7.5), 6.80 (d, 1, J=7.5), 6.70 (m, 3), 3.70 (s, 3), 2.90 (t, 2, J=7.4), 2.65 (t, 2, J=7.4).

3-(3-Hydroxy-3-methylbutyl)phenol

Ester 42 (19.4 g, 108 mmol) is treated with MeMgBr according to general procedure A. The crude product (MW= 259.2) is purified by crystallization from cyclohexane/ $CH_2Cl_2$ (1:1) to afford a white powder, 19.0 g (98%). $^1$H NMR (CDCl$_3$) 7.15 (t, 1, J=7.3), 6.80 (d, 1, J=7.3), 6.65 (m, 2), 4.90 (s, 1), 2.65 (m, 2), 1.80 (m, 2), 1.30 (s, 6).

4-Bromo-3-(3-hydroxy-3-methylbutyl)phenol

The phenol from the previous reaction (19.0 g, 105 mmol) is brominated by the same procedure used to brominate phenol 29. The crude product is purified by crystallization from cyclohexane/EtOAc to give 20.0 g (73%) of white crystals. $^1$H NMR (DMSO-d$_6$, 2.50 ppm) 9.54 (s, 1), 7.29 (d, 1, J=8.6), 6.69 (d, 1, J=2.9), 6.53 (dd, 1, J=8.6, 2.9), 4.27 (s, 1), 2.65–2.55 (m, 2), 1.60–1.50 (m, 2), 1.14 (s, 6); $^{13}$C NMR (DMSO-d$_6$, 39.43 ppm) 156.98, 142.73, 132.90, 117.08, 114.98, 111.99, 68.61, 43.94, 30.88, 29.13; MS (MW=259.2, EI, eE=70 eV) m/z 260/258 (M$^+$), 243, 241 (base peak), 187, 185.

4-Bromo-3-(3-hydroxy-3-methylbutyl)-2,6-(bispyrrolidin-1-ylmethyl)phenol

The bromophenol from the previous step (20.0 g, 77.2 mmol) is aminomethylated as described above for compound 30. The crude product, an orange oil (33.0 g, 103%), is used without further purification. $^1$H NMR (CDCl$_3$) 7.17 (s, 1), 3.83 (s, 2), 3.70 (s, 2), 2.95–2.90 (m, 2), 2.60–2.55 (m, 8), 1.85–1.70 (m, 10), 1.23 (s, 6); $^{13}$C NMR (CDCl$_3$) 156.43, 141.31, 131.17, 123.65, 122.68, 113.40, 69.91, 56.96, 53.46, 53.26, 51.54, 42.53, 29.38, 27.34, 23.55, 23.27; MS (MW= 425.4, CI/CH$_4$, eE=70 eV) m/z 427/425 [(M$^+$H)$^+$, base peak], 426/424 (M$^+$), 409, 407, 356, 354, 338, 336, 326, 324, 84.

3-(3-Hydroxy-3-methylbutyl)-2,6-bis[(4-methoxybenzyl-sulfanyl)methyl]phenol

The bis(pyrrolidine) compound from the previous reaction (6.32 g, 14.8 mmol) is treated with 4-methoxybenzyl mercaptan as described above for compound 32. The (bis) sulfide is obtained as an orange oil (3.9 g, 41%) after FC (CH$_2$Cl$_2$, then 9:1 CH$_2$Cl$_2$/CH$_3$CN). $^1$H NMR (CDCl$_3$) 7.25–7.15 (m, 4), 6.88 (d, 1, J=7.8), 6.85–6.80 (m, 4), 6.68 (d, 1, J=7.8), 3.79 (apparent s, 8), 3.75 (s, 2), 3.65 (s, 2), 3.57 (s, 2), 2.65–2.55 (m, 2), 1.70–1.65 (m, 2), 1.33 (br s, 1), 1.22 (s, 6); $^{13}$C NMR (CDCl$_3$) 158.65, 153.93, 142.17, 130.18, 130.00, 129.91, 129.53, 129.39, 122.94, 121.19, 120.77, 113.93, 113.89, 70.76, 55.24, 45.39, 36.36, 34.80, 31.88, 29.10, 27.67, 27.18; MS (MW=512.7, CI/CH$_4$, eE=70 eV) m/z 513 (M$^+$H)$^+$, 495, 360, 359, 341, 121 (base peak)

3-(3-Hydroxy-3-methylbutyl)-2,6-dimethylphenol

The (bis)sulfide from the previous reaction (17.1 g, 33.4 mmol) is desulfurated as described above for compound 33. The product is obtained as a light orange paste (5.0 g, 72%) after FC (CH$_2$Cl$_2$, then 9:1 CH$_2$Cl$_2$/CH$_3$CN). $^1$H NMR (CDCl$_3$) 6.91 (d, 1, J=7.5), 6.69 (d, 1, J=7.5), 4.63 (s, 1), 2.70–2.65 (m, 2), 2.22 (s, 3), 2.21 (s, 3), 1.70–1.65 (m, 1), 1.58 (s, 1), 1.31 (s, 6); $^{13}$C NMR (CDCl$_3$) 152.11, 139.77, 127.66, 121.18, 120.83, 120.23, 70.90, 44.78, 29.18, 28.39, 15.76, 11.20; MS (MW=207.3, EI, eE=70 eV) m/z 208 (M$^+$), 191, 177, 163, 149, 135 (base peak).

3,3,6,8-Tetramethyl-4,5-dihydro-3H-benzo[c]azepin-7-ol

The product from the previous reaction (4.9 g, 24 mmol) is treated with NaCN as described above for compound 38. The resulting crude, cyclized imine is purified by FC (19:1 CH$_2$Cl$_2$/MeOH, then 9:1 CH$_2$Cl$_2$/MeOH) to afford a dark orange semi-solid (370 mg, 8%). $^1$H NMR (CDCl$_3$) 7.50 (s, 1), 7.00 (s, 1), 3.34 (br s, 1), 3.00–2.95 (m, 2), 2.18 (s, 3), 2.13 (s, 3), 2.00–1.95 (m, 2), 1.41 (s, 6); $^{13}$C NMR (CDCl$_3$) 173.41, 156.30, 143.13, 141.14, 127.66, 125.74, 112.00, 57.81, 36.79, 28.50, 28.41, 16.73, 12.38; MS (MW=217.3, EI, eE=70 eV) m/z 217 (M$^+$), 161 (base peak)

3,3,6,8-Tetramethyl-1,2,4,5-tetrahydro-3H-benzo[c]azepin-7ol

The imine from the previous reaction (356 mg, 1.64 mmol) is reduced with NaBH$_4$ according to general procedure D. The amine (MW=219.3, 256 mg, 71%) is used in the next step without purification. $^1$H NMR (CDCl$_3$) 6.74 (s, 1), 3.84 (s, 2), 2.85–2.80 (m, 2), 2.21 (s, 3), 2.18 (s, 3), 1.65–1.60 (m, 2), 1.21 (s, 6); $^{13}$C NMR (CDCl$_3$) 151.02, 139.57, 134.02, 128.02, 121.43, 119.49, 100.68, 53.68, 47.56, 39.80, 25.01, 15.69, 11.91.

3,3,6,8-Tetramethyl-4,5-dihydro-3H-benzo[c]azepin-7-ol, N-oxide (16)

The amine from the previous reaction (250 mg, 1.14 mmol) is oxidized according to general procedure E. The nitrone 16 is obtained as a tan powder (104 mg, 39%). $^1$H NMR (CDCl$_3$) 7.79 (s, 1), 6.82 (s, 1), 6.03 (br s, 1), 2.95–2.90 (m, 2), 2.23 (s, 3), 2.22 (s, 3), 2.15–2.10 (m, 2), 1.58 (s, 6); $^{13}$C NMR (CDCl$_3$) 153.66, 140.65, 138.65, 132.69, 122.37, 121.46, 120.66, 70.76, 37.56, 27.47, 26.43, 15.81, 11.89; MS (MW=233.3, CI/CH$_4$, eE=70 eV) m/z 234 [(M$^+$H)$^+$, base peak], 233, 218, 201, 176.

EXAMPLE 9

6,6-Dimethyl-6,7-dihydrothieno[3,2-c]pyridine N-oxide (48)

3-Thiophen-2-yl-2,2-dimethylpropionic acid ethyl ester (44)

Ethyl isobutyrate (10.9 mL, 81.7 mmol) is alkylated with 2-(chloromethyl)thiophene according to general procedure F to give the product 44 as a yellow liquid (16.4 g, 95%). $^1$H NMR (CDCl$_3$) 7.15–7.10 (m, 1), 6.95–6.90 (m, 1), 6.77 (d, 1, J=3.6), 4.15 (t, 2, J=7.0), 3.07 (s, 2), 1.26 (t, 3, J=7.0), 1.21 (s, 6); $^{13}$C NMR (CDCl$_3$) 176.96, 139.80, 126.74, 126.42, 123.94, 60.59, 43.65, 40.30, 25.07, 14.22; MS (MW=212.3, CI/CH$_4$, eE=70 eV) m/z 213 [(M$^+$H)$^{30}$, base peak], 193, 179, 167, 140, 139, 125, 98, 97.

3-Thiophen-2-yl-2,2-dimethylpropionic acid (45)

Ester 44 (16.4 g, 77.2 mmol) is hydrolyzed according to general procedure G to give 45 as a milky liquid (11.0 g, 77%). $^1$H NMR (CDCl$_3$) 7.15 (d, 1, J=5.1), 6.95–6.90 (m, 1), 6.83 (d, 1, J=3.4), 3.10 (s, 2), 1.26 (s, 6); $^{13}$C NMR (CDCl$_3$) 183.98, 139.37, 127.05, 126.66, 124.19, 43.55, 39.86, 24.69; MS (MW=184.3, EI, eE=70 eV) m/z 184 (M$^+$), 139, 123, 97 (base peak), 77, 69, 53, 45.

2-(2-Isocyanato-2-methylpropyl)-thiophene (46)

The carboxylic acid from the previous reaction (11.0 g, 60.0 mmol) is subjected to the Curtius rearrangement according to general procedure H to give the isocyanate 46 as a pale yellow liquid (9.94 g, 92%). $^1$H NMR (CDCl$_3$) 7.22 (d, 1, J=5.1), 6.99 (, 6.89 (d, 1, J=3.5), 3.00 (s, 2), 1.38 (s, 6); $^{13}$C NMR (CDCl$_3$) 138.20, 127.58, 126.74, 124.80, 58.12, 43.77, 29.92; IR (CHCl$_3$) 2982, 2259, 1265, 1167, 704; MS (MW=181.3, EI, eE=70 eV) m/z 181 (M$^+$), 149, 138, 127, 123, 99, 97 (base peak), 84, 77, 71, 58, 45.

6,6-Dimethyl-6,7-dihydro-5H-thieno[3,2-c]pyridin-4-one (47)

To a mixture of dry DCE (60 mL) and anhydrous H$_3$PO$_4$ (35 mL, prepared from 85% H$_3$PO$_4$ and P$_2$O$_5$) is added a solution of isocyanate 46 (5.12 g, 28.3 mmol) in DCE (20 mL). The resulting mixture is stirred vigorously at rt for 2 h, then at reflux for 4 h. The reaction mixture is allowed to cool and separate into two layers. The upper, organic layer is decanted, diluted with EtOAc and Na$_2$Co$_3$ solution, and extracted with EtOAc (2x). The organic extract is washed with brine (2x) and dried (MgSO$_4$), filtered, and evaporated. The residue is purified by FC (6:4 CH$_2$Cl$_2$/CH$_3$CN) to give a yellow solid, mp 153–154° C. Yield: 2.10 g (41%). $^1$H NMR (CDCl$_3$) 7.43 (d, 1, J=5.2), 7.10 (d, 1, J=5.2), 6.82 (s, 1), 2.99 (s, 2), 1.38 (s, 6); $^{13}$C NMR (CDCl$_3$) 162.64, 144.99, 130.86, 125.70, 122.96, 54.00, 37.31, 29.05; MS (EI, eE=70 eV) m/z 181 (M$^+$), 166, 151, 148, 125, 124 (base peak), 96, 83, 70, 45; Anal. Calcd for C$_9$H$_{11}$NOS (MW= 181.3): C, 59.64 H, 6.12 N, 7.73. Found: C, 59.76 H, 6.17 N, 7.87.

6,6-Dimethyl-4,5,6,7-tetrahydrothieno[3,2-c]pyridine

Lactam 47 (2.76 g, 15.2 mmol) is reduced according to general procedure I to give a dark liquid (MW=167.3, 1.82 g, 71%). $^1$H NMR (CDCl$_3$) 7.07 (d, 1, J=5.1), 6.75 (d, 1, J=5.1), 3.93 (s, 2), 2.66 (s, 2), 1.64 (br s, 1), 1.21 (s, 6).

6,6-Dimethyl-6,7-dihydrothieno[3,2-c]pyridine N-oxide (48)

The amine from the previous reaction (1.82 g, 10.9 mmol) is oxidized according to general procedure E to give the nitrone 48 as a yellow solid (660 mg, 33%, mp 130–131° C.) after recrystallization from 4:1 hexane/CH$_2$Cl$_2$. $^1$H NMR (CDCl$_3$) 7.72 (s, 1), 7.17 (d, 1, J=5.1), 6.89 (d, 1, J=5.1), 3.15 (s, 2), 1.50 (s, 6); $^{13}$C NMR (CDCl$_3$) 131.24, 130.31, 128.63, 124.73, 123.54, 67.87, 37.41, 24.99; MS (EI, eE=70 eV) m/z 181 (M$_+$, base peak), 166, 149, 138, 134, 110, 96, 91, 77, 65, 51, 45; Anal. Calcd for C$_9$H$_{11}$NOS (MW=181.3): C, 59.64 H, 6.12 N, 7.73. Found: C, 59.45 H, 6.22 N, 7.67.

EXAMPLE 10

5,5-Dimethyl-4,5-dihydrofuro[2,3-c]pyridine N-oxide (53)

3-Furan-3-yl-2,2-dimethylpropionic acid ethyl ester

Ethyl isobutyrate (10.7 mL, 80.1 mmol) is alkylated with 3-(chloromethyl)furan according to general procedure F to give the product as a yellow liquid (12.91 g, 82%) after FC (CH$_2$Cl$_2$). $^1$H NMR (CDCl$_3$) 7.32 (s, 1), 7.20 (s, 1), 6.20 (s, 1), 4.12 (t, 2, J=7.4), 2.66 (s, 2), 1.25 (t, 3, J=7.4), 1.18 (s, 6); 13C NMR (CDCl$_3$) 177.56, 142.36, 140.54, 120.78, 112.76, 60.39, 42.85, 35.43, 24.96, 14.13; MS (MW=196.3, CI/CH$_4$, eE=70 eV) m/z 197 (M$_+$H)$_+$, 195, 161, 151, 123 (base peak), 109, 81.

3-Furan-3-yl-2,2-dimethylpropionic acid

The ester from the previous reaction (12.9 g, 65.8 mmol) is hydrolyzed according to general procedure G to give a yellow liquid (10.24 g, 93%) after FC (CH$_2$Cl$_2$). $^1$H NMR (CDCl$_3$) 7.34 (s, 1), 7.24 (s, 1), 6.25 (s, 1), 2.69 (s, 2), 1.22 (s, 6); 13C NMR (CDCl$_3$) 184.25, 142.38, 140.60, 120.34, 112.14, 42.99, 35.27, 24.81; MS (MW=168.2, EI, eE=70 eV) m/z 168 (M$^+$), 123, 81 (base peak), 53.

3-(2-Isocyanato-2-methylpropyl)-furan

The carboxylic acid from the previous reaction (10.2 g, 60.7 mmol) is subjected to the Curtius rearrangement according to general procedure H to give the isocyanate (8.56 g, 85%) as a yellow liquid. $^1$H NMR (CDCl$_3$) 7.39 (s, 1), 7.31 (s, 1), 6.34 (s, 1), 2.63 (s, 2), 1.34 (s, 6); $^{13}$C NMR (CDCl$_3$) 142.66, 140.96, 128.32, 119.64, 58.00, 39.35, 29.99; IR (film) 2962, 2930, 2257, 2172, 2135, 1717, 1489, 1208, 1186, 1163, 963; MS (MW=165.2, EI, eE=70 eV) m/z 168 (M$^+$), 123, 81 (base peak), 53.

5,5-Dimethyl-5,6-dihydro-4H-furo[2,3-c]pyridin-7-one (51)

To a solution of BF$_3$.Et$_2$O (2 mL, 160 mmol) in dry DCE (60 mL) at rt under N$_2$ is added a solution of isocyanate (6.60 g, 40.0 mmol) in DCE (20 mL) dropwise over 20 min. Stirring at rt is continued for 5 h. The reaction mixture is quenched by adding ice-cold NaHCO$_3$ solution. The mixture is diluted with EtOAc, washed with NaHCO$_3$ solution, dried (MgSO$_4$), filtered, and concentrated. The residue is crystallized from EtOAc to provide 51(2.19 g, 33%) as a pale yellow solid, mp 133–134° C. $^1$H NMR (CDCl$_3$) 7.53 (d, 1, J=1.8), 6.37 (d, 1, J=1.8), 5.50 (br s, 1), 2.77 (s, 2), 1.38 (s, 6); $^{13}$C NMR (CDCl$_3$) 159.15, 146.02, 128.42, 111.71, 110.72, 54.83, 35.07, 29.35; MS (EI, eE=70 eV) m/z 165 (M$_+$), 150 (base peak), 132, 122, 108, 94, 80, 52, 42; Anal. Calcd for C$_9$H$_{11}$NO$_2$ (MW=165.2) : C, 65.44 H, 6.71 N, 8.48. Found: C, 65.33 H, 6.81 N, 8.42.

5,5-Dimethyl-4,5,6,7-tetrahydrofuro[2,3-c]pyridine

The lactam from the previous reaction (5.60 g, 3.39 mmol) is reduced according to general procedure I to give a dark liquid (MW=151.3, 2.46 g, 48%)which is not characterized, but used directly in the next step.

5,5-Dimethyl-4,5-dihydrofuro[2,3-c]pyridine N-oxide (53)

The amine from the previous reaction (2.42 g, 16.0 mmol) is oxidized according to general procedure E. The nitrone 53 is obtained as a yellow solid (1.35 g, 51%, mp 89–90° C.) after FC (3:2 CH$_2$Cl$_2$/CH$_3$CN). $^1$H NMR (CDCl$_3$) 7.68 (s, 1), 7.42 (s, 1), 6.40 (s, 1), 2.89 (s, 2), 1.48 (s, 6); $^{13}$C NMR (CDCl$_3$) 145.01, 143.97, 124.05, 115.30, 110.91, 69.52, 34.67, 29.68, 25.45; MS (EI, eE=70 eV) m/z 165 (M$^+$, base peak), 150, 148, 133, 122, 105, 95, 91,79, 77, 66, 65, 53, 51, 41; Anal. Calcd for C$_9$H$_{11}$NO$_2$ (MW=165.2): C, 65.44 H, 6.71 N, 8.48. Found: C, 65.43 H, 6.70 N, 8.51.

EXAMPLE 11

6-Methoxy-1,1-dimethyl-1H-isoindole N-oxide (58)

2-(3-Methoxyphenyl)-2-methylpropionitrile (54)

To an ice-cold slurry of NaH (17.69 g, 60% dispersion in mineral oil, 440 mmol) in THF (500 mL) is added a solution of 3-methoxyphenylacetonitrile (25.0 g, 170 mmol) in THF (25 mL) over 30 min. The mixture is stirred for 30 min, then a solution of CH$_3$I (55.5 g, 390 mmol) in THF (25 mL) is added over 30 min. The reaction mixture is allowed to reach rt and stirring is continued until GC analysis indicates complete reaction (25 min). The reaction mixture is poured into cold water/EtOAc, the layers are separated, and the aqueous phase is extracted again with EtOAc. The organic phase is washed with brine, dried (MgSO$_4$), filtered, and evaporated to give the product 54 (MW=175.2) as a dark liquid, 31.0 g (104%) which is used without purification. $^1$H NMR (CDCl$_3$) 7.31 (t, 1, J=8.1), 7.05–7.00 (m, 2), 6.90–6.85 (m, 1), 3.83 (s, 3), 1.72 (s, 6).

2-(3-Methoxyphenyl)-2-methylpropionic acid (55)

Crude nitrile 54 (23.12 g, 132.1 mmol) is hydrolyzed according to general procedure G to afford the carboxylic acid 55 as a pale yellow solid, mp 46–47° C., 20.76 g (81%) $^1$H NMR (CDCl$_3$) 7.24 (t, 1, J=8.0), 7.00–6.95 (m, 2), 6.85–6.80 (m, 1), 3.81 (s, 3), 1.58 (s, 6); $^{13}$C NMR (CDCl$_3$) 182.90, 159.57, 145.44, 129.40, 118.27, 112.41, 111.68, 55.19, 46.24, 26.14; MS (MW=194.2, CI/CH$_4$, eE=70 eV) m/z 195 (M$^+$H)$^+$, 194, 177, 150, 149 (base peak), 137, 121, 109.

1-(1-Isocyanato-1-methylethyl)-3-methoxybenzene (56)

Carboxylic acid 55 (23.12 g, 132.1 mmol) is submitted to the Curtius rearrangement according to general procedure H to give isocyanate 56 (MW=191.2), as a yellow liquid. The crude product (16.84 g, 96%) is used in the next step without purification. $^1$H NMR (CDCl$_3$) 7.26 (t, 1, J=8.2), 7.00 (m, 2), 6.85–6.80 (m, 1), 3.80 (s, 3), 1.69 (s, 6); $^3$C NMR (CDCl$_3$) 159.64, 147.56, 129.52, 116.70, 112.02, 111.06, 60.71, 55.26, 32.97.

5-Methoxy-3,3-dimethyl-2,3-dihydroisoindol-1-one (57), and 7-Methoxy-3,3-dimethyl-2,3-dihydroisoindol-1-one (61)

To an ice-cold slurry of FeCl$_3$ (35.69 g, 220 mmol) in dry DCE (800 mL) is added a solution of isocyanate 56 (19.12 g, 100.0 mmol) in the same solvent (100 mL) over 45 min. After completion of the addition, GC analysis of an aliquot indicates complete reaction. Water (600 mL) is added and the resulting mixture is stirred vigorously. The layers are separated, and the organic phase is washed 2×1 L with 1 M tartaric acid solution and once with brine. The solution is dried (MgSO$_4$), filtered and evaporated to a dark liquid. This is purified by FC (1:4 hexane/EtOAc, then EtOAc) to provide the 5-methoxy isoindolone 57 as a pale yellow solid, mp 146–147° C., 7.38 g (39%), and the regioisomeric 7-methoxy isoindolone 61 as a yellow solid, mp 155–158° C., 2.85 g (15%). For 57: $^1$H NMR (CDCl$_3$) 7.74 (d, 1, J=8.5), 7.00–6.95 (m, 1), 6.85 (d, 1, J=2.2), 3.89 (s, 3), 1.54 (s, 6); $^{13}$C NMR (CDCl$_3$) 169.57, 163.19, 155.44, 125.31, 123.14, 114.18, 105.92, 58.64, 55.61, 27.81; MS (MW= 191.2, EI, eE=70 eV) m/z 191 (M$^+$), 176 (base peak), 161, 133, 118, 88, 77, 63, 42.

For 61: $^1$H NMR (CDCl$_3$) 7.51 (t, 1, J=8.0), 6.95 (d, 1, J=8.0), 6.88 (d, 1, J=8.0), 6.28 (br s, 1), 3.98 (s, 3), 1.51 (s,

6); $^{13}$C NMR (CDCl$_3$) 168.58, 157.58, 156.10, 133.84, 131.35, 112.90, 109.90, 57.94, 55.86, 27.90; MS (MW= 191.2, EI, eE=70 eV) m/z 191 (M$^+$), 176 (base peak), 162, 158, 133, 118, 103, 89, 63, 42.

6-Methoxy-1,1-dimethyl-1H-isoindole N-oxide (58)

Lactam 57 from the previous reaction (170 mg, 0.889 mmol) is reduced according to general procedure I to furnish the amine as a colorless liquid which is not purified or characterized. The crude material (177 mg, 1.00 mmol) is oxidized according to general procedure E. The nitrone 58 is obtained as a pale yellow solid (54 mg, 28%, mp 119–122° C.) after FC (97:3 CH$_2$Cl$_2$/iPrOH). $^1$H NMR (CDCl$_3$) 7.61, (s, 1), 7.29 (d, 1, J=8.4), 6.90–6.85 (m, 1), 6.84 (d, 1, J=2.3), 3.86 (s, 3), 1.56 (s, 6); $^{13}$C NMR (CDCl$_3$) 160.14, 147.60, 131.44, 124.87, 121.15, 113.50, 107.90, 55.61, 24.54; MS (MW=191.2, EI, eE=70 eV) m/z 191 (M$^+$, base peak), 176, 158, 145, 131, 115, 103, 91, 89, 77, 63, 51, 43.

EXAMPLE 12

6-Hydroxy-1,1-dimethyl-1H-isoindole N-oxide (64)
5-Hydroxy-3,3-dimethyl-2,3-dihydroisoindol-1-one (62)

A 1 M solution of BBr$_3$ in CH$_2$Cl$_2$ (88.0 mL, 88.0 mmol) is dissolved in dry CH$_2$Cl$_2$ under N$_2$. A solution of lactam 57 (7.65 g, 40.0 mmol) in CH$_2$Cl$_2$ (50 mL) is added to the BBr$_3$ solution dropwise over 10 min. The resulting mixture is stirred at rt overnight. The reaction mixture is poured into water and extracted with EtOAc (3×). The organic phase is dried (MgSO$_4$), filtered, and evaporated, leaving the product 62 as a white solid (4.03 g, 57%), mp 231–233° C., which requires no purification. $^1$H NMR (DMSO-d$_6$, 2.50 ppm) 8.18 (s, 1), 7.28 (d, 1, J=8.5), 6.75 (d, 1, J=1.6), 6.67 (dd, 1, J=8.5, 1.6), 1.25 (s, 6); $^{13}$C NMR (CDCl$_3$+DMSO-d$_6$) 169.30, 161.06, 155.40, 124.68, 121.53, 115.39, 107.26, 57.98, 27.47; MS (MW=177.2, EI, eE=70 eV) m/z 177 (M$^+$), 163, 162 (base peak).

6-Hydroxy-1,1-dimethyl-2,3-dihydro-1H-isoindole, hydrochloride

Lactam 62 (1.42 g, 8.01 mmol) is reduced according to general procedure I, except that the HCl extract is simply evaporated to furnish the amine hydrochloride salt (MW= 199.7). Residual water can be removed by repeatedly dissolving the residue in CH$_3$CN and evaporating the mixture. A white solid (1.6 g, 100%) is obtained which is not purified further. $^1$H NMR (CDCl$_3$+DMSO-d$_6$) 8.98 (vbr s, 2), 6.95 (d, 1, J=9.0), 6.59 (d, 1, J=9.0), 6.55 (s, 1), 4.02 (s, 2), 1.32 (s, 6); $^{13}$C NMR (DMSO-d$_6$, 39.43 ppm) 156.96, 143.44, 122.24, 121.19, 111.55, 106.44, 66.51, 45.56, 24.32.

6-Hydroxy-1,1-dimethyl-1H-isoindole N-oxide (64)

The amine hydrochloride from the previous reaction (615 mg, 3.08 mmol) is oxidized according to general procedure E except that 1.0 equivalent of NaOH is added to generate the free amine in situ. The nitrone 64 is obtained as a white solid (60 mg, 11%, mp 225–230° C.) after FC (EtOAc). $^1$H NMR (DMSO-d$_6$, 2.50 ppm) 9.48 (s, 1), 7.70 (s, 1), 7.20 (d, 1, J=8.0), 6.82 (d, 1, J=2.2), 6.80–6.75 (m, 1), 1.50 (s, 6); $^{13}$C NMR (DMSO-d$_6$, 39.43 ppm) 157.54, 147.18, 130.00, 120.95, 114.99, 109.09, 76.01, 24.10; MS (MW=177.2, EI, eE=70 eV) m/z 177 [(M$^+$), base peak], 162, 144, 131, 115, 91, 89, 77, 63, 51, 43.

EXAMPLE 13

1,1-dimethyl-1H-isoindole N-oxide (65)
3,3-Dimethyl-5-(1-phenyl-1H-tetrazol-5-yloxy)-2,3dihydroisoindol-1-one A solution of lactam 62 (1.77 g, 10.0 mmol) and 5-chloro-1phenyl-1H-tetrazole (2.17 g, 12.0 mmol) in dry DMF (50 mL) is treated with solid K$_2$CO$_3$ (2.07 g, 15.0 mmol). The mixture is stirred overnight at rt, then poured into water and extracted with EtOAc (2×). The organic phase is washed with water (3×) and brine (2×), then dried (MgSO$_4$), filtered, and evaporated. The residue is crystallized from CH$_2$Cl$_2$ to give a white solid, mp 202–204° C. The material weighs 3.10 g (97% yield). $^1$H NMR (CDCl$_3$) 7.90 (d, 1, J=8.3), 7.80 (m, 2), 7.60–7.55 (m, 4), 7.50–7.45 (m, 1), 6.78 (s, 1), 1.59 (s, 6); $^{13}$C NMR (CDCl$_3$) 168.45, 158.80, 156.15, 155.27, 132.83, 129.81, 128.77, 125.78, 122.33, 119.44, 112.11, 59.14, 53.39, 27.59; MS (MW=321.3, EI, eE=70 eV) m/z 321 (M$^+$), 306, 293, 278, 261, 250, 236, 222, 208, 187, 176, 161 (base peak), 145, 133, 117, 103, 91, 77, 65, 42.

3,3-Dimethylisoindol-1-one (63)

The product from the previous reaction (3.10 g, 9.65 mmol) is dissolved in EtOH (80 mL), and hydrogenated over 5% Pd/C (400 mg) at 50 psi H$_2$ on a Parr shaker overnight at rt. The catalyst is filtered off, and the solvent evaporated. The residue is purified by PC (Et$_2$O) to furnish 63 as a white solid, mp 159–160° C. The product (1.03 g) is obtained in 66% yield. $^1$H NMR (CDCl$_3$) 7.83 (d, 1, J=7.6), 7.57 (t, 1, J-=7.6), 7.45–7.40 (m, 2), 1.57 (s, 6); $^{13}$C NMR (CDCl$_3$) 169.94, 153.17, 131.96, 130.74, 127.89, 123.76, 120.82, 59.10, 27.65; MS (MW=161.2, EI, eE=70 eV) m/z 161 (M$^+$), 146 (base peak), 128, 103, 91, 77, 65, 51, 42.

1,1-dimethyl-2,3-dihydro-1H-isoindole, hydrochloride

Lactam 63 (1.42 g, 8.01 mmol) is reduced according to general procedure I, except that the HCl extract is simply evaporated to furnish the amine hydrochloride salt (MW= 183.7). Residual water can be removed by repeatedly dissolving the residue in CH$_4$CN and evaporating the mixture. A white solid (918 mg, 100%) is obtained which is not purified further. $^1$H NMR (CDCl$_3$+DMSO-d$_6$) 10.30 (br s, 2), 7.40–7.35 (m, 3), 7.25–7.20 (m, 1), 4.55 (s, 2), 1.76 (s, 6); $^{13}$C NMR (CDCl$_3$+DMSO-d6) 132.02, 128.10, 127.90, 122.26, 120.25, 110.43, 60.98, 46.78, 25.51.

1,1-dimethyl-1H-isoindole N-oxide (65)

The amine hydrochloride from the previous reaction (918 mg, 5.00 mmol) is oxidized according to general procedure E except that 1.0 equivalent of NaOH is added to generate the free amine in situ. The nitrone 65 is obtained as a white solid (113 mg, 14%, mp 64–65° C.) after PC (8:2 CH$_2$Cl$_2$/CH$_3$CN). $^1$H NMR (CDCl$_3$) 7.66 (s, 1), 7.36 (m, 3), 7.27 (m, 1), 1.57 (s, 6); $^3$C NMR (CDCl$_3$) 145.43, 132.33, 131.50, 128.36, 127.54, 120.68, 120.12, 77.62, 24.46; MS (CI/CH$_4$, eE=70 eV) m/z 162 [(M$^+$H)$^+$, base peak], 144, 128; Anal. Calcd for C$_{10}$H$_{11}$NO (MW=161.2): C, 74.51 H, 6.88 N, 8.69. Found: C, 74.29 H, 6.92 N, 8.64.

EXAMPLE 14

4-Methoxy-1,1-dimethyl-1H-isoindole N-oxide
4-Methoxy-1,1-dimethyl-2,3-dihydro-1H-isoindole, hydrochloride Lactam 61 [see example 11] (1.19 g, 6.22 mmol) is reduced according to general procedure I, except that the HCl extract is simply evaporated to furnish the amine hydrochloride salt (MW=213.7). Residual water can be removed by repeatedly dissolving the residue in CH$_3$CN and evaporating the mixture. A white solid (1.33 g, 100%) is obtained which is not purified further. $^1$H NMR (CDCl$_3$ +DMSO-d$_6$) 10.26 (br s, 2), 7.35 (t, 1, J=7.7), 6.85–6.75 (m, 2), 4.47 (br s, 2), 3.86 (s, 3), 1.74 (s, 6); $^{13}$C NMR (CDCl$_3$+DMSO-d$_6$) 143.55, 129.51, 124.98, 118.85, 111.64, 108.88, 67.38, 53.91, 44.16, 24.20

4-Methoxy-1,1-dimethyl-1H-isoindole N-oxide

The amine hydrochloride from the previous reaction (1.33 g, 6.21 mmol) is oxidized according to general procedure E except that 1.0 equivalent of NaOH is added to generate the free amine in situ. The nitrone is obtained as a yellow solid (190 mg, 16%, mp 149–152° C.) after FC (EtOAc). $^1$H NMR (CDCl$_3$) 7.74 (s, 1), 7.35–7.25 (m, 1), 6.88 (d, 1, J=8.9), 6.84 (d, 1, J=8.9), 3.90 (s, 3), 1.55 (s, 6); $^{13}$C NMR (CDCl$_3$) 152.12, 147.15, 129.29, 129.14, 113.28, 110.16, 77.78, 55.52, 24.46; MS (MW=191.2, EI, eE=70 eV) m/z 191 [(M$^+$), base peak], 176, 158, 134, 131, 128, 115, 91, 77, 65, 63, 51, 43.

EXAMPLE 15

3,3-Dimethyl-3,4-dihydroisoquinolin-4-ol, N-oxide (C)

1-Methoxy-3-(1-methyl-1-nitroethyl)-1,3dihydroisobenzofuran (71).

Sodium metal (12.4 g, 0.539 g atm) is added to MeOH, (1 L) at 10° C. over 90 min. When a clear solution is obtained the cold water bath is removed and 2-nitropropane (256 mL, 2.85 mol) is added, followed by orthophthalaldehyde (120 g, 0.895 mol). The resulting solution is stirred at rt overnight. The solution is acidified by adding 1 N H$_2$SO$_4$ to pH 2. White solids precipitate. The mixture is filtered, and the filter cake is washed with MeOH and discarded. The filtrate is stirred at rt for 3 h and then made basic by adding 3 N NaOH. The solution is then concentrated in vacuo to remove the MeOH. The resulting aqueous solution is extracted twice with Et$_2$O. The combined organic layers are washed once with water, dried (MgSO$_4$) and concentrated in vacuo. Kugelrohr distillation of remaining solvent at 50° C. (oil pump vacuum) leaves 195 g (106% of theoretical, 86% pure by GC) of a brown liquid, which is used as such in the next step. The ratio of diastereoisomers is 1:1 ($^1$H NMR). A portion of the crude material can be purified by flash chromatography over silica gel (9:1 cyclohexane/EtOAc) to give pure 71 as a pale yellow oil. $^1$H NMR(CDCl$_3$) 7.42–7.36(m, 3), 7.17–7.12(m, 1), 6.25 and 5.88(isomer I, d and dd, 1 total, J=2.4, 0.6, respectively), 6.01 and 5.72 (isomer II, s and d, 1 total, J=0.6), 3.58 and 3.37 (isomers I and II, respectively, 2s, 3 total), 1.57 and 1.56 and 1.55 and 1.48 (4s, 6 total); $^{13}$C NMR (CDCl$_3$) 138.77, 138.51, 137.57, 129.82, 129.67, 129.21, 129.13, 123.41, 122.09, 107.32, 107.01, 90.52, 86.77, 56.14, 54.03, 22.51, 22.14, 21.73, 20.96; IR (neat) 1543, 1464, 1398, 1373, 1348, 1113, 1094, 1026, 974, 756;MS, m/z 206 [(M+H)+, base peak], 190, 149; Anal. Calcd for C$_{12}$H$_{15}$NO$_2$: C,60.75; H,6.37; N,5.90. Found: C,60.48; H,6.28;N,6.00.

N-[1-(3-Methoxy-1,3-dihydroisobenzofuran-1-yl)-1-methylethyl]-hydroxylamine (72).

Aluminum foil (Reynolds, 1.29 g, 0.048 g atm) is torn into strips and each strip is amalgamated by immersing it in a solution of mercury(II) chloride (2.0 g) in water (100 mL) for 15 s. Each strip is then rinsed successively with anhydrous EtOH and Et$_2$O, and then added to Et$_2$O(100 mL) and water (0.6 mL, 33 mmol) in a three-necked, round bottom flask. A solution of 1(4.8 g, 23.0 mmol) in Et$_2$O (50 mL) is then added to the stirred mixture from a dropping funnel at a rate to maintain a vigorous reflux. The bubbling which occurs initially subsides within 30 min. The mixture is filtered and the filtrate washed twice with 2 N NaOH, dried (MgSO$_4$) and concentrated in vacuo to obtain a pale green oil (4.6 g, 88%). Flash chromatography over silica gel (1:1 EtOAc/cyclohexane) gives recovered starting material (0.48 g, 10%), and the hydroxylamine 2 as a pale green glass (2.24 g, 43%). $^1$H NMR (CDCl$_3$) 7.39–7.31(m, 4), 6.28 and 5.55 (isomer I, 2d,1 total, J=2.4), 6.03 and 5.41 (isomer II, 2s, 1 total), 3.62 and 3.34 (isomers I and II, respectively, 2s, 3 total), 1.32 and 0.88 (isomer II, 2s, 3 total), 1.27 and 0.80 (isomer I, 2s, 3 total) $^{13}$C NMR (CDCl$_3$) for one isomer, 140.06, 138.22, 129.17, 128.07, 123.16, 122.34, 106.51, 85.64, 61.10, 53.16, 20.44, 19.07; d for other isomer, 139.70, 138.47, 129.06, 127.96, 123.13, 122.27, 106.99, 60.32, 56.10, 20.95, 19.43; IR (CHCl$_3$) 2980, 2934, 2907, 2891, 1375, 1111, 1092, 1015, 974, 752; MS, m/z 224(M+H)$^+$, 192, 149, 119 (base peak), 74.

3,3-Dimethyl-3,4-dihydroisoquinolin-4-ol, N-oxide (C)

To a solution of 72 (7.1 g, 31.8 mmol) in THF(20 mL) is added 2 N HCl (10 mL) and the resulting solution is stirred for 45 min at room temperature. More 2 N HCl (10 mL) is added, and the solution is stirred for 30 min. The solution is slowly poured into a saturated aqueous NaHCO$_3$solution and extracted 5 times with EtOAc. The combined organic layers are dried (MgSO$_4$) and concentrated in vacuo to obtain 6.1 g of yellow oil. Recrystallization from EtOAc/cyclohexane gives 3.45 g (57%) of cream crystals, mp 134–136° C. A second crop (0.62 g, 10%) can be obtained by evaporating the mother liquor, and recrystallizing the residue from hexane/CH$_2$Cl$_2$, bringing the total yield to 67 %. $^1$H NMR (CDCl$_3$) 7.62 (s, 1), 7.47–7.45 (m, 1), 7.38–7.30 (m, 2), 7.12–7.09 (m, 1), 4.58 (d, 1, J=6.3), 3.93 (d, 1, J=6.3), 1.47 (s, 3), 1.36 (s, 3); $^{13}$C NMR (CDCl$_3$) 132.81, 132.72, 129.82, 128.86, 127.28, 126.56, 125.15, 74.71, 71.55, 23.31, 19.02; IR (KBr) 3154, 3028, 1562, 1370, 1269, 1236, 1169, 1057, 777; MS m/z 192 [(M+H)$^+$, base peak), 174 ; Anal. Calcd. for C$_{11}$H$_{13}$NO$_2$: C, 69.09; H, 6.85; N, 7.32. Found: C, 68.99; H, 6.89; N, 7.19.

EXAMPLE 16

4-Acetoxy-3,3-dimethyl-3,4-dihydroisoquinoline, N-oxide (76)

To a solution of MDL 104,824 (3.3 g, 17 mmol) in CH$_2$Cl$_2$ (100 mL) are added Et$_3$N (3.1 mL, 22 mmol), 4-dimethylaminopyridine (210 mg, 1.7 mmol), and Ac$_2$O (1.8 mL, 19 mmol). The mixture is stirred for 1 h at rt, then poured into water and extracted with CH$_2$Cl$_2$ (2×). The organic phase is dried (MgSO$_4$), filtered, and evaporated to give a yellow paste. This is purified by FC (9:1 CH$_2$Cl$_2$/acetone) to afford 1.83 g of a pale yellow solid. Recrystallization from cyclohexane/EtOAc provides 76 as cream crystals (1.53 g, 38%). $^1$H NMR (CDCl$_3$) 7.76 (s, 1), 7.45–7.25 (m, 3), 7.20–7.15 (m, 1), 5.89 (s, 1), 2.02 (s, 3), 1.57 (s, 3), 1.36 (s, 3); IR (KBr) 3048, 2986, 2936, 1734, 1593, 1553, 1454, 1375, 1287, 1240, 1211, 1018, 978, 964, 770; MS (EI, eE=70 eV) m/z 233 [(M$^+$), base peak], 191, 190, 174, 156, 143, 130, 115, 91, 89, 77, 63, 51, 43; Anal. Calcd for C$_{13}$H$_{15}$NO$_3$ (MW=233.3): C, 66.94 H, 6.48 N, 6.00. Found: C, 66.95 H, 6.36 N, 5.97.

EXAMPLE 17

3,3-Dimethyl-3H-isoquinolin-4-one, N-oxide (77)

To a solution of MDL 104,824 (3.22 g, 16.8 mmol) in CH$_2$Cl2 (150 mL) under N$_2$ is added dimethyl sulfoxide (23.8 mL, 336 mmol). The resulting solution is cooled to −45° C. Oxalyl chloride (11.4 mL, 131 mmol) is added over 10 min, such that the internal temperature remains below −40° C. The mixture is stirred and maintained between −55° C. and −40° C. for 2 h. iPr$_2$NEt (44 mL, 250 mmol) is added over 15 min, such that the internal temperature remains below −50° C. The reaction mixture is then allowed to warm to rt, whereupon it is poured into water and extracted with CH$_2$Cl$_2$ (2×). The organic phase is washed with brine, dried (MgSO$_4$), filtered, and concentrated to give a yellow oil. The material is filtered through silica gel (EtOAc) and crystallized from cyclohexane/EtOAc to furnish 77 as a yellow powder (2.0 g, 63%). $^1$H NMR (CDCl$_3$) 8.07 (d+fine coupling, 1, J=7.8), 7.86 (s, 1), 7.69 (dt, 1, J=7.6, 1.3), 7.49 (dt, 1, J=7.6, 1.0), 7.31 (d+fine coupling, 1, J=7.8), 1.74 (s, 6); IR (KBr) 3048, 2996, 1680, 1601, 1555, 1487, 1377, 1366, 1300, 1281, 1244, 1179, 891, 872, 758, 660; MS (EI, eE=70 eV) m/z 191, 189 [(M$^+$), base peak], 172, 158, 145, 144, 130, 115, 104, 89, 77, 63, 51; Anal. Calcd for C$_{13}$H$_{15}$NO$_3$ (MW=189.2): C, 69.83 H, 5.86 N, 7.40. Found: C, 69.86 H, 5.86 N, 7.36.

EXAMPLE 18

3,4-dihydroisoquinolin-4-ol-3-spirocyclohexane, N-oxide (D)

1-Methoxy-3-(1-nitrocyclohexyl)-1,3-dihydroisobenzofuran (a)

Sodium metal (0.46 g, 0.02 g-atom) is added to MeOH (35 mL) portionwise at rt. When a homogeneous solution is obtained, nitrocyclohexane (12.92 g, 100 mmol) is added, followed by o-phthalaldehyde (8.38 g, 60.0 mmol). The resulting solution is stirred at rt overnight. The solution is brought to pH 2 by adding 1 N H$_2$SO$_4$ and stirred at rt for 60 min. White solids precipitate. The mixture is filtered, and the filtrate, from which an oil separates, is made basic by adding 10% NaOH solution. The solution is concentrated in vacuo to remove the MeOH, and the resulting aqueous solution is extracted twice with Et$_2$O. The combined organic layers are washed once with brine, dried (MgSO$_4$), filtered, and concentrated. After final drying on a vacuum pump, a yellow oil is obtained (17.29 g, 100%). The following data were obtained on a ca. 1:1 mixture of the cis and trans diastereoisomers. $^1$H NMR (CDCl3) 7.45–7.35 (m, 3), 7.20–7.10 (m, 1), 6.26 and 5.55 (isomer I, 2 d, 1 total, J=2.7, and 2.3 Hz, respectively), 5.98 and 5.38 (isomer II, 2 s, 1 total), 3.59 and 3.36 (isomers I and II, respectively, 2s, 3 total), 2.59 (m, 2), 2.22 (m, 2), 1.95–1.10 (m, 6).

N-[1-(3-Methoxy-1,3-dihydroisobenzofuran-1-yl)-1cyclohexyl]-hydroxylamine (b)

Aluminum amalgam (from 6 g of aluminum foil) is prepared as described previously and added to a mixture of Et$_2$O(600 mL) and water (1.5 mL, 83 mmol) in a three-necked, round bottom flask. A solution of the nitroacetal from the previous reaction (14.24 g, 51.4 mmol) in Et$_2$O (60 mL) is then added to the stirred mixture from a dropping funnel at a rate to maintain a vigorous reflux. The bubbling which occurs initially subsides within 30 min. The mixture is filtered and the filtrate washed with 1 N NaOH and brine, dried (MgSO4), filtered, and concentrated to afford a yellow oil. Flash chromatography over silica gel (1:1 EtOAc/hexane) gives the hydroxylamine b as a pale yellow oil (7.19 g, 53%). The following data were obtained on a ca. 1:1 mixture of the cis and trans diastereoisomers. $^1$H NMR (CDCl3) 7.45–7.30 (m, 4), 6.28 and 5.55 (isomer I, 2d,1total, J=1.4), 6.03 and 5.41 (isomer II, 2s, 1 total), 3.62 and 3.34 (isomers I and II, respectively, 2s, 3 total), 1.32 and 0.88 (isomer II, 2s, 3 total), 1.27 and 0.80 (isomer I, 2s, 3 total) $^{13}$C NMR (CDCl$_3$) for one isomer, 140.06, 138.22, 129.17, 128.07, 123.16, 122.34, 106.51, 85.64, 61.10, 53.16, 20.44, 19.07; for other isomer, 139.70, 138.47, 129.06, 127.96, 123.13, 122.27, 106.99, 60.32, 56.10, 20.95, 19.43; IR (CHCl$_3$) 2980, 2934, 2907, 2891, 1375, 1111, 1092, 1015, 974, 752; MS (CI/CH$_4$, eE=120 eV), m/z 264 (M+H)$^+$, 262, 246, 230, 214, 199, 171, 150, 149, 135, 118, 114 (base peak), 96, 84.

3,4-dihydroisoquinolin-4-ol-3-spirocyclohexane, N-oxide (D)

To a solution of b (7.19 g, 27.3 mmol) in THF (100 mL) is added 10% HCl (50 mL) and the resulting solution is stirred for 20 min at rt. The solution is then slowly poured into a saturated aqueous NaHCO$_3$ solution and extracted 3 times with EtOAc. The combined organic layers are dried (MgSO$_4$), filtered, and concentrated, whereupon a beige solid precipitates. This is collected and washed with hexane to furnish 3.36 g (53%) of pure product. The filtrate is evaporated, and the residue crystallizes from EtOAc/hexane to give a second crop (0.72 g, 11%) of product, bringing the total yield to 64%. Mp 195–197° C. $^1$H NMR (CDCl$_3$) 7.65 (s, 1), 7.45–7.30 (m, 3), 7.20–7.10 (m, 1), 4.93 (d, 1, J=7.3), 3.32 (d, 1, J=7.3), 2.47 (td, 1, J=16.0, 4.9), 2.25–2.15 (m, 1), 2.00–1.85 (m, 1), 1.80–1.30 (m, 7); $^{13}$C NMR (CDCl$_{13}$) 132.37, 131.55, 129.63, 129.25, 128.66, 126.87, 125.13, 74.22, 69.65, 32.01, 26.21, 24.99, 22.60, 22.07; IR (KBr) 3408, 3073, 3052, 2980, 2938, 2926, 2857, 1593, 1553, 1454, 1414, 1260, 1235, 1179, 1161, 1107, 1049, 1030, 912, 851, 764, 613; MS (CI/CH$_4$, eE=120 eV), m/z 232 [(M+H)$^+$, base peak], 214, 198, 183; Anal. Calcd for C$_{14}$H$_{17}$NO$_2$ (MW=231.3): C, 72.70; H, 7.41; N, 6.06. Found: C, 72.92; H, 7.24; N, 5.93.

EXAMPLE 19

3H-isoquinolin-4-one-3-spirocyclohexane, N-oxide, (E)

To a solution of oxalyl chloride (0.50 mL, 5.73 mmol) in CH$_2$Cl$_2$ (15 mL) at –78° C. under N$_2$ is added a solution of dimethyl sulfoxide (1 mL, 14.1 mmol) in CH$_2$Cl$_2$ (5 mL). The resulting solution is stirred for 5 min at –78° C. D from the previous reaction (1.16 g, 5.00 mmol) is dissolved in warm DMSO and then allowed to cool to rt. This solution is added to the reagent solution at a rate such that the internal temperature remains below –40° C. The mixture is stirred and maintained in the –78° C. bath for 15 min, then treated with a solution of Et$_3$N (3.5 mL, 25 mmol) in CH$_2$Cl$_2$ (7 mL) at a rate such that the internal temperature remains below –50° C. The mixture is stirred and maintained in the –78° C. bath for 15 min, then allowed to warm to rt. The reaction mixture is poured into water and extracted with CH$_2$Cl$_2$ (2×). The organic phase is washed with brine, dried (MgSO$_4$), filtered, and concentrated. The residue is crystallized from hexane/EtOAc to furnish E as yellow needles (0.85 g, 74%). Mp 92–93° C. $^1$H NMR (CDCl$_3$) 8.03 (d, 1, J=7.7), 7.89 (s, 1), 7.66 (t, 1, J=7.6), 7.48 (t, 1, J=7.6), 7.28 (d, 1, J=7.5), 2.55–2.35 (m, 2), 2.15–1.65 (m, 6), 1.60–1.35 (m, 2); $^{13}$C NMR (CDCl$_1$) 196.96, 135.25, 132.19, 129.64, 127.22, 125.39, 125.27, 111.06, 80.19, 31.92, 24.02, 21.30; IR (KBr) 3441, 3040, 2942, 2884, 2868, 2845, 1694, 1599, 1553, 1447, 1366, 1319, 1281, 1258, 1182, 1157, 882, 752, 696, 660, 637; MS (EI, eE=70 eV) m/z 229 (M$^+$), 213, 212 (base peak), 188, 184, 174, 158, 132, 129, 102, 89, 76, 63, 51, 41; Anal. Calcd for C$_{14}$H$_{15}$NO$_2$ (MW=229.3): C, 73.34; H, 6.59; N, 6.11. Found: C, 73.50; H, 6.58; N, 6.07.

EXAMPLE 20

3,4-dihydroisoquinolin-4-ol-3-spirocyclopentane, N-oxide (F)

1-Methoxy-3-(1-nitrocyclopentyl)-1,3-dihydroisobenzofuran (e).

Condensation of nitrocyclopentane (5.00 g, 40.0 mmol) with o-phthalaldehyde (3.76 g, 28.0 mmol) in the presence of freshly prepared sodium methoxide (10 mmol) in MeOH is carried out as described above for compound a. The resulting pale green oil (7.21 g, 98%) is pure enough for use in the next step. The following data were obtained on a ca. 1:1 mixture of the cis and trans diastereoisomers. $^1$H NMR (CDCl3) 7.50–7.25 (m, 3), 7.10–7.00 (m, 1), 6.16 and 5.91 (isomer I, 2 d, 1 total, J=2.3), 5.93 and 5.80 (isomer II, s and d, respectively, 1 total, J=0.7 Hz), 3.49 and 3.30 (isomers I and II, respectively, 2 s, 3 total), 2.50–2.35 (m, 1), 2.30–1.90 (m, 3), 1.75–1.50 (m, 4); IR (film) 1543, 1464, 1398, 1373, 1348, 1113, 1094, 1026, 974, 756; MS (CI/CH$_4$, eE=120 eV), m/z 236 (M–H)$^+$, 219, 206, 191, 175, 159, 149 (base peak), 131, 118, 91, 73; Anal. Calcd for C$_{12}$H$_{15}$NO$_2$ (MW=237.3): C, 60.75; H, 6.37; N, 5.90. Found: C, 60.48; H, 6.28; N, 6.00.

N-[1-(3-Methoxy-1,3-dihydroisobenzofuran-1-yl)-1cyclopentyl]-hydroxylamine (f).

The nitroacetal e from the previous reaction (7.21 g, 27.5 mmol) is reduced with aluminum amalgam (from 3.31 g of aluminum foil) as described above for compound b. Purification by flash chromatography (1:1 EtOAc/hexane) provides recovered starting material (3.65 g, 35%), and the oily hydroxylamine f (4.14 g, 42%). $^1$H NMR (CDCl$_3$) 7.40–7.30 (m, 4), 6.28 and 5.55 (isomer I, 2d,1 total, J=2.4), 6.03 and 5.41 (isomer II, 2s, 1 total), 3.62 and 3.34 (isomers I and II, respectively, 2s, 3 total), 1.32 and 0.88 (isomer II, 2s, 3 total), 1.27 and 0.80 (isomer I, 2s, 3 total) $^{13}$C NMR (CDCl$_3$) for one isomer, 140.06, 138.22, 129.17, 128.07, 123.16, 122.34, 106.51, 85.64, 61.10, 53.16, 20.44, 19.07; for other isomer, 139.70, 138.47, 129.06, 127.96, 123.13, 122.27, 106.99, 60.32, 56.10, 20.95, 19.43; IR (CHCl$_3$) 2980, 2934, 2907, 2891, 1375, 1111, 1092, 1015, 974, 752; MS (CI/CH$_4$, eE=120 eV), m/z 250 (M+H)$^+$, 248, 246, 218, 200, 185, 172, 149, 135, 119, 100 (base peak), 84, 67.

3,4-dihydroisoquinolin-4-ol-3-spirocyclopentane, N-oxide (F)

Hydroxylamine f(4.14 g, 16.7 mmol) is converted into nitrone F according to the procedure described above for D. The product (1.87 g, 52%) is obtained as a white solid after chromatography over silica gel (EtOAc/hexane, then EtOAc). Mp 141–143° C. $^1$H NMR (CDCl$_3$) 7.67 (s, 1), 7.45–7.30 (m, 3), 7.15–7.10 (m, 1), 4.52 (d, 1, J=7.3), 3.98 (d, 1, J=7.3), 2.70–2.55 (m, 1), 2.15–2.05 (m, 1), 2.00–1.50 (m, 6); $^{13}$C NMR (CDCl$_3$) 132.67, 132.52, 129.58, 129.08, 127.80, 127.16, 125.16, 82.15, 74.29, 36.56, 30.54, 26.60, 25.86; IR (KBr) 3397, 3385, 3351, 3196, 3117, 3067, 3000, 2959, 2872, 1595, 1561, 1452, 1397, 1254, 1240, 1171, 1119, 1101, 1063, 1030, 772; MS (EI, eE=70 eV), m/z 218, 217 (M$^+$), 200 (base peak), 176, 170, 142, 130, 115, 104, 89, 77, 51, 41; Anal. Calcd for C$_{13}$H$_{15}$NO$_2$ (MW=217.3): C, 71.87; H, 6.96; N, 6.45. Found: C, 71.99; H, 6.98; N, 6.58.

EXAMPLE 21

3H-isoquinolin-4-one-3-spirocyclopentane, N-oxide, (G)

F (1.09 g, 5.02 mmol) is oxidized with DMSO (1.0 mL, 14.1 mmol), oxalyl chloride (0.5 mL, 5.73 mmol) and Et3N (3.5 mL, 25 mmol) according to the procedure described above for D (MDL 105,809). The crude product is purified by two crystallizations from hexane/EtOAc to furnish G as a yellow solid (0.65 g, 60%). Mp 107–108° C. $^1$H NMR (CDCl$_3$) 8.06 (d, 1, J=7.8), 7.88 (s, 1), 7.68 (t, 1, J=7.6), 7.47 (t, 1, J=7.6), 7.30 (d, 1, J=7.8), 2.55–2.45 (m, 2), 2.35–1.90 (m, 6); $^{13}$C NMR (CDCl$_3$) 197.89, 135.60, 132.12, 132.03, 129.61, 127.17, 125.71, 125.01, 86.91, 40.42, 27.82; IR (KBr) 3441, 2976, 2945, 2870, 1682, 1595, 1555, 1485, 1360, 1323, 1281, 1252, 1181, 893, 855, 756, 662; MS (EI, eE=70 eV) m/z 215 (M$^+$), 198 (base peak), 174, 170, 152, 130, 127, 103, 89, 76, 63, 41; Anal. Calcd for C$_{13}$H$_{13}$NO$_2$ (MW=215.3): C, 72.54; H, 6.09; N, 6.51. Found: C, 72.53; H, 6.09; N, 6.48.

What is claimed is:

1. The compound which is 2,2-dimethyl-1,2-dihydrobenzo[f]isoquinoline N-oxide.

2. The compound which is 3,3-dimethyl-3,4-dihydrobenzoiso[h]quinoline N-oxide.

3. The compound which is 5,5-dimethyl-4,5-dihydrothieno[2,3-c]pyridine N-oxide.

4. The compound which is 5,5-dimethyl-4,5-dihydrofuro[2,3-c]pyridine N-oxide.

5. The compound which is 6,6-dimethyl-6,7-dihydrothieno[3,2-c]pyridine N-oxide.

6. A compound which is 3,3-dimethyl-3,4-dihydroisoquinolin-4-ol N-oxide.

7. A compound which is 4-acetoxy-3,3-dimethyl-3,4-dihydroisoquinoline N-oxide.

8. A compound which is 3,3-dimethyl-3H-isoquinoline-4-one N-oxide.

9. A method for treating oxidative tissue damage comprising administering to a patient in need thereof a protective amount of a compound according to any one of claims 1–8, either alone or in combination.

10. A method for the treatment of stroke comprising administering to a patient in need thereof a protective amount of a compound according to any one of claims 1–8, either alone or in combination.

11. A method for the treatment of myocardial infarction comprising administering to a patient in need thereof a protective amount of a compound according to any one of claims 1–8, either alone or in combination.

12. A method for the treatment of neurodegenerative disease comprising administering to a patient in need thereof a protective amount of a compound according to any one of claims 1–8, either alone or in combination.

13. A method for the treatment of shock comprising administering to a patient in need thereof a protective amount of a compound according to any one of claims 1–8, either alone or in combination.

14. A method for treatment of tissue damage associated with physical trauma involving excessive bleeding comprising administering to a patient in need thereof a protective amount of a compound according to any one of claims 1–8, either alone or in combination.

15. A method for treatment of artherosclerosis involving excessive bleeding comprising administering to a patient in need thereof a protective amount of a compound according to any one of claims 1–8, either alone or in combination.

16. A pharmaceutical composition comprising a compound according to any one of claims 1–8, either alone or in combination, present in an effective amount in admixture with a pharmaceutically acceptable carrier.

* * * * *

UNITED STATES PATENT AND TRADEMARK OFFICE
CERTIFICATE OF CORRECTION

PATENT NO. : 5,962,469

DATED : October 5, 1999

INVENTOR(s) : Criag E. Thomas; Thomas L. Fevig, Stephen M. Bowen, Robert A. Farr, Albert A. Carr and David A. Janowick It is certified that error appears in the above-identified patent and that said Letters Patent is hereby corrected as shown below:

Column 3, Line 4 reads "alkyl,  and the ring" and should read --alkyl, OH, OAc or 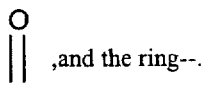 ,and the ring--.

Column 16, Line 61 reads "StarkeReed," and should read --Starke-Reed,--.

Column 28, Line 19 reads "exane" and should read --hexane--.

Column 29, Line 4 reads "13C" and should read --$^{13}$C--.

Column 29, Line 23 reads "5 Cyclization" and should read --Cyclization--.

Column 29, Line 28 reads "13C" and should read --$^{13}$C--.

Column 30, Line 19 reads "a. 75:25" and should read --ca. 75:25--.

Column 30, Line 21 reads "re" and should read --are--.

Column 30, Line 30 reads "EI,eE=70" and should read --EI, eE=70--.

Column 30, Line 40 reads "13C" and should read --$^{13}$C--.

Column 31, Line 44 reads "H" and should read --$^1$H--.

Column 32, Line 61 reads "$^{13}$H" and should read --$^1$H--.

Column 33, Line 41 reads "13C" and should read --$^{13}$C--.

Column 33, Line 46 reads "benzo[c]3azepin" and should read --benzo[c]azepin--.

UNITED STATES PATENT AND TRADEMARK OFFICE
CERTIFICATE OF CORRECTION

PATENT NO. : 5,962,469

DATED : October 5, 1999

INVENTOR(s) : Craig E. Thomas et al

It is certified that error appears in the above-identified patent and that said Letters Patent is hereby corrected as shown below:

Column 33, Line 52 reads "13C" and should read --$^{13}$C--.

Column 34, Line 47 reads "–1 yl" and should read ---1–yl--.

Column 36, Line 18 reads "13C" and should read --$^{13}$C--.

Column 38, Line 3 reads "-C" and should read --$^{13}$C--.

Column 38, Line 19 reads "[(M$^+$H)$^{30}$," and should read --[ (M$^+$H)$^+$,--.

Column 39, Line 19 reads "13C" and should read --$^{13}$C--.

Column 39, Line 28 reads "13C" and should read --$^{13}$C--.

Column 40, Line 41 reads "$^3$C" and should read --$^{13}$C--.

Column 41, Line 65 reads "3dihydro" and should read --3-dihydro--.

Column 41, Line 67 reads "1phenyl" and should read --1-phenyl--.

Column 42, Line 42 reads "PC" and should read --FC--.

Column 42, Line 44 reads "$^3$C" and should read --$^{13}$C--.

Column 43, Line 14 reads "3dihydro" and should read --3-dihydro--.

Column 45, Line 31 reads "(CDC13)" and should read --(CDCl$_3$)--.

Column 45, Line 37 reads "1cyclohexyl" and should read --1-cyclohexyl--.

Column 45, Line 47 reads "(MgSO4)" and should read --(MgSO$_4$)--.

Column 45, Line 52 reads "(CDC13)" and should read --(CDCl$_3$)--.

Column 45, Line 53 reads "1total" and should read --1 total--.

Column 46, Line 12 reads "(CDCl$_{13}$)" and should read --(CDCl$_3$)--.

UNITED STATES PATENT AND TRADEMARK OFFICE
CERTIFICATE OF CORRECTION

PATENT NO. : 5,962,469

DATED : October 5, 1999

INVENTOR(s) : Craig E. Thomas, et al

It is certified that error appears in the above-identified patent and that said Letters Patent is hereby corrected as shown below:

Column 47, Line 12 reads "1cyclopentyl" and should read -- –1–cyclopentyl--.

Column 48, Line 11 reads "dihydrobenzoiso[h]quinoline" and should read --dihydrobenzo[h]isoquinoline--.

Signed and Sealed this

Seventeenth Day of April, 2001

Attest:

NICHOLAS P. GODICI

*Attesting Officer*    *Acting Director of the United States Patent and Trademark Office*